(12) United States Patent
Makin et al.

(10) Patent No.: US 10,295,500 B2
(45) Date of Patent: May 21, 2019

(54) ELECTRO-ACOUSTIC SENSORS FOR REMOTE MONITORING

(71) Applicant: UltraPower Inc., New York, NY (US)

(72) Inventors: Inder Raj S. Makin, Mesa, AZ (US); Harry Jabs, Oakland, CA (US); Leon J. Radziemski, Tucson, AZ (US)

(73) Assignee: UltraPower Inc., New York, NY (US)

( * ) Notice: Subject to any disclaimer, the term of this patent is extended or adjusted under 35 U.S.C. 154(b) by 0 days.

(21) Appl. No.: 15/679,876

(22) Filed: Aug. 17, 2017

(65) Prior Publication Data

US 2017/0363581 A1 Dec. 21, 2017

Related U.S. Application Data

(63) Continuation-in-part of application No. 15/457,109, filed on Mar. 13, 2017, now Pat. No. 9,764,606,
(Continued)

(51) Int. Cl.
*G01N 29/24* (2006.01)
*G01N 29/04* (2006.01)
(Continued)

(52) U.S. Cl.
CPC ........... *G01N 29/04* (2013.01); *B06B 1/0207* (2013.01); *B60C 23/0469* (2013.01);
(Continued)

(58) Field of Classification Search
CPC ......... G01N 29/04; G01N 29/24; H02J 50/80; H02J 50/10; H02J 50/15; H02J 50/40;
(Continued)

(56) References Cited

U.S. PATENT DOCUMENTS 4,784,147 A 11/1988 Moshfeghi
5,554,922 A 9/1996 Kunkel
(Continued)

OTHER PUBLICATIONS

S. Ozeri et al., "Ultrasonic transcutaneous energy transfer for powering implanted devices", Ultrasonics, 2010, p. 556-566, vol. 50, Elsevier.
(Continued)

*Primary Examiner* — Lisa M Caputo
*Assistant Examiner* — Rose M Miller
(74) *Attorney, Agent, or Firm* — Intrinsic Law Corp.

(57) ABSTRACT

Ultrasonic transmitting elements in an electroacoustical transceiver transmit acoustic energy to an electroacoustical transponder, which includes ultrasonic receiving elements to convert the acoustic energy into electrical power for the purposes of powering one or more sensors that are electrically coupled to the electroacoustical transponder. The electroacoustical transponder transmits data collected by the sensor(s) back to the electroacoustical transceiver wirelessly, such as through impedance modulation or electromagnetic waves. A feedback control loop can be used to adjust system parameters so that the electroacoustical transponder operates at an impedance minimum. An implementation of the system can be used to collect data in a vehicle, such as the tire air pressure. Another implementation of the system can be used to collect data in remote locations, such as in pipes, enclosures, in wells, or in bodies of water.

15 Claims, 32 Drawing Sheets

Related U.S. Application Data which is a continuation-in-part of application No. 14/671,741, filed on Mar. 27, 2015, now Pat. No. 9,627,919.

(60) Provisional application No. 61/971,204, filed on Mar. 27, 2014.

(51) Int. Cl.
| | |
|---|---|
| *H04B 11/00* | (2006.01) |
| *B06B 1/02* | (2006.01) |
| *H02J 7/02* | (2016.01) |
| *H02J 50/15* | (2016.01) |
| *H02J 7/00* | (2006.01) |
| *B60C 23/04* | (2006.01) |
| *H02J 50/10* | (2016.01) |
| *H02J 50/40* | (2016.01) |
| *H02J 50/80* | (2016.01) |

(52) U.S. Cl.
CPC ............ *G01N 29/24* (2013.01); *H02J 7/0042* (2013.01); *H02J 7/0047* (2013.01); *H02J 7/025* (2013.01); *H02J 50/10* (2016.02); *H02J 50/15* (2016.02); *H02J 50/40* (2016.02); *H02J 50/80* (2016.02); *H04B 11/00* (2013.01); *B06B 2201/51* (2013.01); *B06B 2201/55* (2013.01)

(58) Field of Classification Search
CPC ........ H02J 7/0042; H02J 7/0047; H02J 7/025; B06B 1/0207; B06B 2201/51; B06B 2201/53; B60C 23/0469
USPC .......................................... 73/632, 622, 623
See application file for complete search history.

(56) References Cited

U.S. PATENT DOCUMENTS

| | | | |
|---|---|---|---|
| 5,659,173 | A | 8/1997 | Putterman et al. |
| 5,889,383 | A | 3/1999 | Teich |
| 6,175,302 | B1 | 1/2001 | Huang |
| 6,342,776 | B1 | 1/2002 | Taylor et al. |
| 6,798,716 | B1 | 9/2004 | Charych |
| 7,839,273 | B2 * | 11/2010 | Tabe .................. B60C 23/0408 340/442 |
| 8,011,237 | B2 | 9/2011 | Gao et al. |
| 8,082,041 | B1 | 12/2011 | Radziemski |
| 8,974,366 | B1 | 3/2015 | Radziemski et al. |
| 9,484,522 | B2 | 11/2016 | Andosca et al. |
| 2005/0254344 | A1 * | 11/2005 | Barras ................... H04B 11/00 367/76 |
| 2010/0027379 | A1 * | 2/2010 | Saulnier ................ G08C 23/02 367/137 |
| 2010/0127833 | A1 * | 5/2010 | Sugano ............... G06Q 10/087 340/10.1 |
| 2012/0299540 | A1 | 11/2012 | Perry |
| 2012/0299541 | A1 | 11/2012 | Perry |
| 2012/0299542 | A1 | 11/2012 | Perry |
| 2012/0300588 | A1 | 11/2012 | Perry |
| 2012/0300592 | A1 | 11/2012 | Perry |
| 2012/0300593 | A1 | 11/2012 | Perry |
| 2013/0241468 | A1 | 9/2013 | Moshfeghi |
| 2013/0241474 | A1 | 9/2013 | Moshfeghi |
| 2014/0016558 | A1 * | 1/2014 | Lawry .................. H04L 5/0046 370/328 |
| 2014/0265725 | A1 | 9/2014 | Angle et al. |
| 2014/0265727 | A1 | 9/2014 | Berte |
| 2014/0265943 | A1 | 9/2014 | Angle et al. |
| 2014/0281655 | A1 | 9/2014 | Angle et al. |
| 2014/0355388 | A1 * | 12/2014 | Kent ..................... H04B 11/00 367/140 |
| 2015/0049587 | A1 * | 2/2015 | Lawry ................... H04B 11/00 367/87 |

OTHER PUBLICATIONS

M. Peisino, "Deeply implanted medical device based on a novel ultrasonic telemetry technology", École Polytechnique Federale de Lausanne, 2013, Thesis No. 5730.

E. Leinov et al., "Investigation of guided wave propagation and attenuation in pipe buried in sand", Journal of Sound and Vibration, Jul. 7, 2015, p. 96-114, vol. 347, Elsevier.

National Oilwell Varco, "Pneumatic Kelly Spinner KS6600 User's Manual", 2007, p. 1-50, Doc. No. 50000865-MAN-001, Varco BJ BV, Netherlands.

D. Yang et al., "Through-Metal-Wall Power Delivery and Data Transmission for Enclosed Sensors: A Review", Sensors, 2015, p. 31581-31605, vol. 15, MDPI.

* cited by examiner

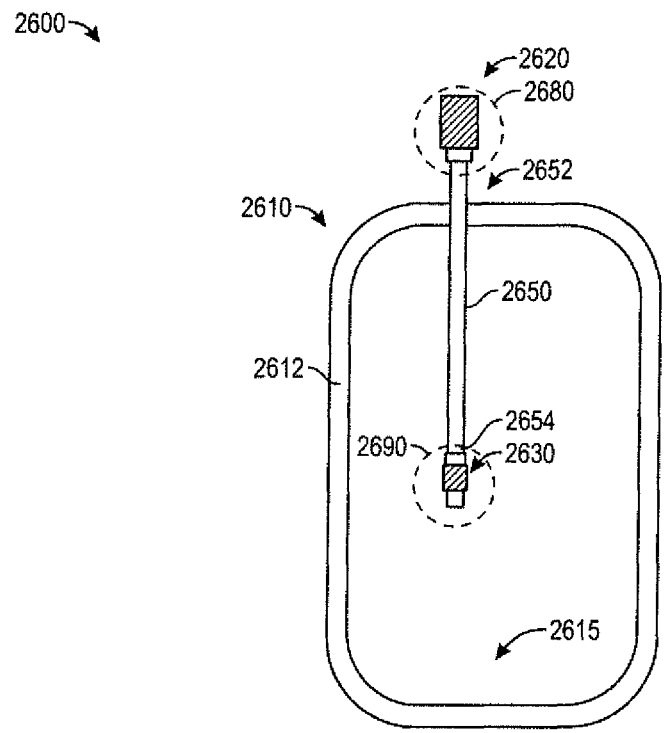
FIG. 26A
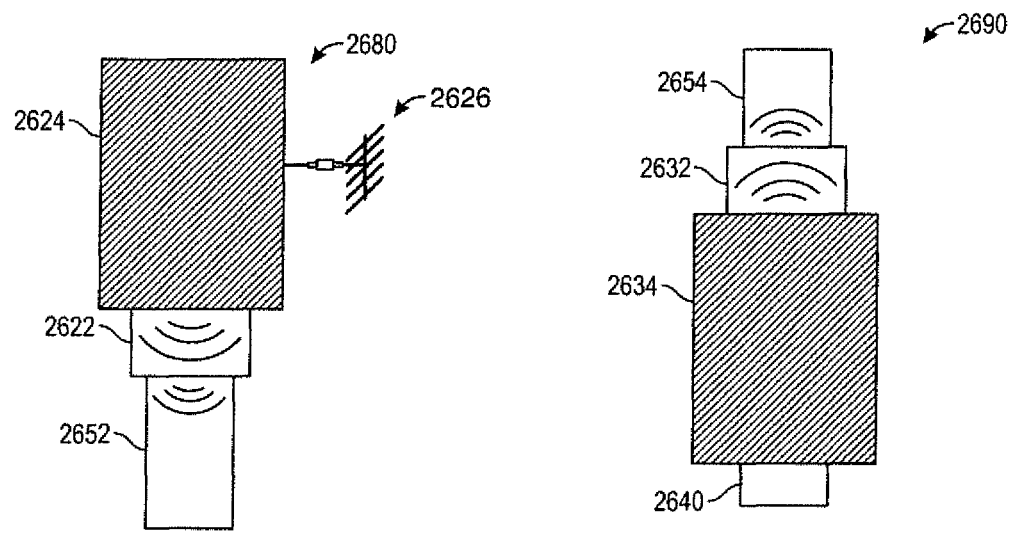
FIG. 26B  FIG. 26C

ELECTRO-ACOUSTIC SENSORS FOR REMOTE MONITORING

RELATED APPLICATIONS

This application is continuation-in-part of U.S. patent application Ser. No. 15/457,109, entitled "Electro-Acoustic Sensors," filed on Mar. 13, 2017, which is a continuation-in-part of U.S. patent application Ser. No. 14/671,741, now U.S. Pat. No. 9,627,919 entitled "Electro-Acoustic Device Charging and Power Supply," filed on Mar. 27, 2015 and issued on Apr. 18, 2017, which claims priority to U.S. Provisional Application No. 61/971,204, entitled "Battery Charging or Direct Power Delivery," filed on Mar. 27, 2014, all of which are hereby incorporated by reference.

TECHNICAL FIELD

This application relates to the transmission of electrical power between electronic devices without the use of wires. More specifically, the present application pertains to the transmission of electrical power to directly power a sensor, such as a sensor in a remote location.

BACKGROUND

Portable devices such as mobile phones, laptop computers, tablets, and other communication device primarily rely on electrical battery energy to operate and conduct communications. Electrical batteries store chemical energy and deliver electrical energy through an electrochemical conversion process. Electrical batteries may be non-rechargeable or rechargeable. Although some portable devices may use non-rechargeable batteries, the vast majority depend on rechargeable batteries.

To recharge, conventional power transfer into portable devices requires these devices to be plugged into an electrical outlet. Although wireless data transmission is commonplace, wireless power transmission is not, except at extremely low power levels and not in an effective form for many applications. One impediment to wireless power transmission is the diffusion and diffraction of electromagnetic waves which is the conventional wireless transmission of electrical power. Consequently, this spreads out the available energy so that only a tiny fraction is available at the receiving end.

Nevertheless, manufacturers have begun producing wireless battery charging stations. They operate under the principle of electromagnetic (EM) induction. electromagnetic induction is well known in the art and involves coupling the magnetic field generated by an external coil with an implanted coil (Schuder, 1960; Van Schuylenbergh and Puers, 2009). As the name connotes, wireless charging pads recharge portable device batteries and forego the necessity of connecting wires.

Other disclosures, e.g., patent Pub. No. US 2013/0241468 A1 (Moshfeghi, 2013) disclose battery charging using an array of transducers and a power combiner connected to a battery charger. These systems are costly and difficult to manufacture and maintain and have other operational limits with respect to the power and frequency range of their operation, which make them non-ideal for some applications as discussed below.

With the proliferation of wireless devices, electromagnetic interference amongst devices will become an increasing problem with electromagnetic induction charging. In general, electromagnetic waves are incoherent and tend to spread out spatially while propagating. Electromagnetic systems also depend on a progressively crowded frequency space shared with other devices. Both electromagnetic stray fields (noise) from diffusion and bandwidth encroachment can interfere with the operation of nearby devices that are sensitive to such interference.

Although a useful method, electromagnetic induction charging has other limitations. To achieve sufficient power at the receiver, the power level at the transmitter becomes impractically high. Additionally, to focus a useable amount of energy to the transmitter requires physically large antennas. This is due to the focusing antennas having to be many times larger than the wavelength of the transmitted radiation.

Furthermore, there is difficulty of controlling the impedance matching as a function of transmitter and receiver alignment. That in turn reduces the efficiency of transmission, leading to heating of the electronic devices themselves, causing, in some cases, their failure. There are also issues relating to safety and electromagnetic interference to other electronic devices.

Therefore, there exists a need for an electric power charging system using directional power propagation without the threat of electromagnetic interference and bandwidth infringement of other devices.

Other problems exist in the automotive industry. For example, underinflated automotive tires are the cause of many avoidable accidents. Since manually checking the tire pressure is inconvenient, it is often neglected by the motorist. Several systems have been developed and deployed to automate this process, but they all have shortcomings. Indirect tire pressure monitoring systems (TPMSs) suffer inaccuracy and are plagued with a high percentage of false positives as well as false negatives. Direct TPMSs (DTPMs) require batteries that must be replaced at regular intervals and are prone to failure due to harsh environmental conditions, such as vibration, shock and extreme temperatures.

Powering of TPMS sensors has been attempted using micro machined electro mechanical systems (MEMS) embedded in the tire assembly with the TPMS. The powering of these MEMS units is based on energy harvesting resulting from the movement of the tires during the automobile's motion. However, these systems have proven to be unreliable as a powering source due to the difficulty in harvesting useful power from relatively unpredictable types of motion during the automobile's movement. Examples of existing TPMSs are disclosed in U.S. Pat. No. 6,175,302, titled "Tire Pressure Sensor Indicator Including Pressure Gauges That Have a Self-Generating Power Capability," U.S. Pat. No. 8,011,237, titled "Piezoelectric Module For Energy Harvesting, Such As In a Tire Pressure Monitoring System," and U.S. Pat. No. 9,484,522, titled "Piezoelectric Energy Harvester Device With Curved Sidewalls, System, And Methods Of Use And Making."

Therefore, there exists a need for more accurate and more reliable systems to automatically check tire pressure on vehicles.

Other problems exist in industries that require monitoring inside metal enclosures, for example when there are harsh conditions (e.g., high temperature, high pressure, radiation, etc.) or the location is difficult to access. To supply power to a sensor in a metal enclosure, a special electrical feedthrough is required. However, such electrical feedthroughs are cumbersome, costly, and they tend to weaken the structural integrity of the metal enclosure. Examples of industries that use such metal enclosures include the oil and gas industry (including offshore oil and gas), chemical diary, nuclear, and food industries.

Therefore, there exists a need for sensors for metal enclosure that do not require electrical feedthroughs.

Further limitations and disadvantages of conventional and traditional approaches will become apparent to one of skill in the art, through comparison of such systems with some aspects of the present invention as set forth in the present disclosure and claims.

SUMMARY

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure will be set forth in the following detailed description of the disclosure when considered in conjunction with the drawings.

In an aspect, the invention is directed to a system for sensing a physical property inside a pipe having a metallic wall. The system comprises a transceiver mounted at a transceiver location on an external surface of the metallic wall, the transceiver comprising: one or more electroacoustic transmitting elements; a signal generator; and an amplifier. The system also comprises a transponder mounted at a transponder location on an internal surface of the metallic wall, the transponder comprising: one or more electroacoustic receiving elements; and a sensor that measures the physical property of an interior environment of the pipe. The electroacoustic transmitting and receiving elements are in bi-directional ultrasonic communication such that the movable transponder is configured to communicate physical sensor data, received from the sensor, to the transceiver.

In one or more embodiments, said transponder is configured to vary an acoustical impedance to communicate the physical sensor data to the transceiver. In one or more embodiments, the transceiver comprises an antenna to electrically communicate with a central processing unit. In one or more embodiments, signals are generated by said signal generator and amplified by said amplifier, said amplified signals are transmitted over said one or more electroacoustic transmitting elements, said one or more electroacoustic transmitting elements generating acoustic energy that passes from said transceiver to said transponder via said metallic wall. In one or more embodiments, the transponder location corresponds to the transceiver location.

In one or more embodiments, said transmitted ultrasonic signals are received by said electroacoustic receiving elements. In one or more embodiments, the transponder converts said transmitted ultrasonic signals into converted electrical energy. In one or more embodiments, the sensor is powered by said converted electrical energy.

In one or more embodiments, the transceiver is configured to generate progressive longitudinal waves, shear waves, or a combination thereof of ultrasonic energy. In one or more embodiments, the transceiver is configured to generate a standing wave of ultrasonic energy. In one or more embodiments, a high-energy node of the standing wave is disposed at the transponder. In one or more embodiments, the one or more electroacoustic transmitting elements are arranged in a convex configuration and the one or more electroacoustic receiving elements are arranged in a concave configuration.

Another aspect of the invention is directed to a system for sensing a physical property inside a vessel having a metallic wall. The system comprises a transceiver mounted on a first end of a metal rod disposed outside of the vessel, the metal rod extending into the vessel, the transceiver comprising: one or more electroacoustic transmitting elements; a signal generator; and an amplifier. The system also comprises a transponder mounted on a second end of the metal rod disposed inside the vessel, the transponder comprising: one or more electroacoustic receiving elements; and a sensor that measures the physical property of an interior environment of the vessel. The electroacoustic transmitting and receiving elements are in bi-directional ultrasonic communication such that the movable transponder is configured to communicate physical sensor data, received from the physical sensor, to the transceiver.

In one or more embodiments, said transponder is configured to vary an acoustical impedance to communicate the physical sensor data to the transceiver. In one or more embodiments, the transceiver comprises an antenna to electrically communicate with a central processing unit.

In one or more embodiments, signals are generated by said signal generator and amplified by said amplifier, said amplified signals are transmitted over said one or more electroacoustic transmitting elements, said one or more electroacoustic transmitting elements generating acoustic energy that passes from said transceiver to said transponder via said metal rod. In one or more embodiments, said transmitted ultrasonic signals are received by said electroacoustic receiving elements. In one or more embodiments, the transponder converts said transmitted ultrasonic signals into converted electrical energy. In one or more embodiments, the sensor is powered by said converted electrical energy.

In one or more embodiments, the transceiver is configured to generate progressive longitudinal waves, shear waves, or a combination thereof of ultrasonic energy. In one or more embodiments, the transceiver is configured to generate a standing wave of ultrasonic energy. In one or more embodiments, a high-energy node of the standing wave is disposed at the transponder.

Another aspect of the invention is directed to a system for providing electrical energy to a sensor disposed in an enclosure having a metallic wall. The system comprises a transceiver mounted at a transceiver location on an external surface of the metallic wall, the transceiver comprising: one or more electroacoustic transmitting elements; a signal generator; and an amplifier. The system also comprises a transponder mounted at a transponder location on an internal surface of the metallic wall, the transponder comprising: one or more electroacoustic receiving elements; and a sensor that measures a physical property of an object disposed in the enclosure. The electroacoustic transmitting and receiving elements are in bi-directional ultrasonic communication such that the movable transponder is configured to communicate physical sensor data, received from the sensor, to the transceiver.

In one or more embodiments, the sensor comprises an RF transponder. In one or more embodiments, the RF transponder is configured to perform a still or moving scan of an interior of the enclosure to sense a shape of the object. In one or more embodiments, the sensor measures a chemical composition, a heat output, or a moisture content of the object.

In one or more embodiments, said transponder is configured to vary an acoustical impedance to communicate the physical sensor data to the transceiver. In one or more embodiments, the transceiver comprises an antenna to electrically communicate with a central processing unit.

In one or more embodiments, signals are generated by said signal generator and amplified by said amplifier, said amplified signals are transmitted over said one or more electroacoustic transmitting elements, said one or more electroacoustic transmitting elements generating acoustic energy that passes from said transceiver to said transponder via said metallic wall. In one or more embodiments, the transponder location corresponds to the transceiver location. In one or more embodiments, said transmitted ultrasonic signals are received by said electroacoustic receiving elements. In one or more embodiments, the transponder converts said transmitted ultrasonic signals into converted electrical energy. In one or more embodiments, the sensor is powered by said converted electrical energy.

In one or more embodiments, the transceiver is configured to generate progressive longitudinal waves, shear waves, or a combination thereof of ultrasonic energy. In one or more embodiments, the transceiver is configured to generate a standing wave of ultrasonic energy. In one or more embodiments, a high-energy node of the standing wave is disposed at the transponder.

Another aspect of the invention is directed to a system for providing power to one or more sensors disposed at a distal end of a drill. The system comprises a transceiver mounted on a Kelly drive body: an array of electroacoustic transmitting elements; a signal generator; and an amplifier. The system also comprises a transponder mounted on a proximal end of a bottom hole assembly, the bottom hole assembly mechanically coupled to the Kelly drive body via a drill string, the transponder comprising: one or more electroacoustic receiving elements; and one or more sensors that measure a physical property proximal to the bottom hole assembly.

In one or more embodiments, said transponder is configured to vary an acoustical impedance to communicate physical sensor data, collected by the one or more sensors, to the transceiver. In one or more embodiments, the transceiver comprises an antenna to electrically communicate with a central processing unit.

In one or more embodiments, signals are generated by said signal generator and amplified by said amplifier, said amplified signals are transmitted over said one or more electroacoustic transmitting elements, said one or more electroacoustic transmitting elements generating acoustic energy that passes from said transceiver to said transponder via said drill string. In one or more embodiments, said transmitted ultrasonic signals are received by said electroacoustic receiving elements. In one or more embodiments, the transponder converts said transmitted ultrasonic signals into converted electrical energy. In one or more embodiments, the one or more sensors are powered by said converted electrical energy.

In one or more embodiments, the transceiver is configured to generate progressive longitudinal waves, shear waves, or a combination thereof of ultrasonic energy. In one or more embodiments, the transceiver is configured to generate a standing wave of ultrasonic energy. In one or more embodiments, a high-energy node of the standing wave is disposed at the transponder.

Another aspect of the invention is directed to a system for providing power to a stationary underwater control station, the system comprising: an autonomous underwater vehicle having a retractable probe; an ultrasound recharging unit disposed distally on the retractable probe, the ultrasound recharging unit comprising: a housing; an ultrasound transmitter; a first electromechanical mating interface; a signal generator; and an amplifier. The system also comprises a stationary control unit deployed in a body of water, the stationary control unit comprising: an ultrasound receiver; and a second electromechanical mating interface. Signals are generated by said signal generator and amplified by said amplifier, said amplified signals are transmitted over said ultrasound transmitter, said ultrasound transmitter generating acoustic energy that passes from said ultrasound transmitter to said ultrasound receiver via said first and second electromechanical mating interfaces.

In one or more embodiments, said first electromechanical mating interface is pressure balanced and oil-filled. In one or more embodiments, the ultrasound receiver converts said transmitted ultrasonic signals into converted electrical energy. In one or more embodiments, said stationary control unit is electrically coupled to a battery. In one or more embodiments, the battery powers an instrument module.

In one or more embodiments, said ultrasound transmitter and ultrasound receiver are in bi-directional ultrasonic communication. In one or more embodiments, said ultrasound receiver is configured to transmit a battery charge status of a battery coupled to the stationary control unit.

IN THE DRAWINGS

For a fuller understanding of the nature and advantages of the present invention, reference is made to the following detailed description of preferred embodiments and in connection with the accompanying drawings, in which.

Figure 6:
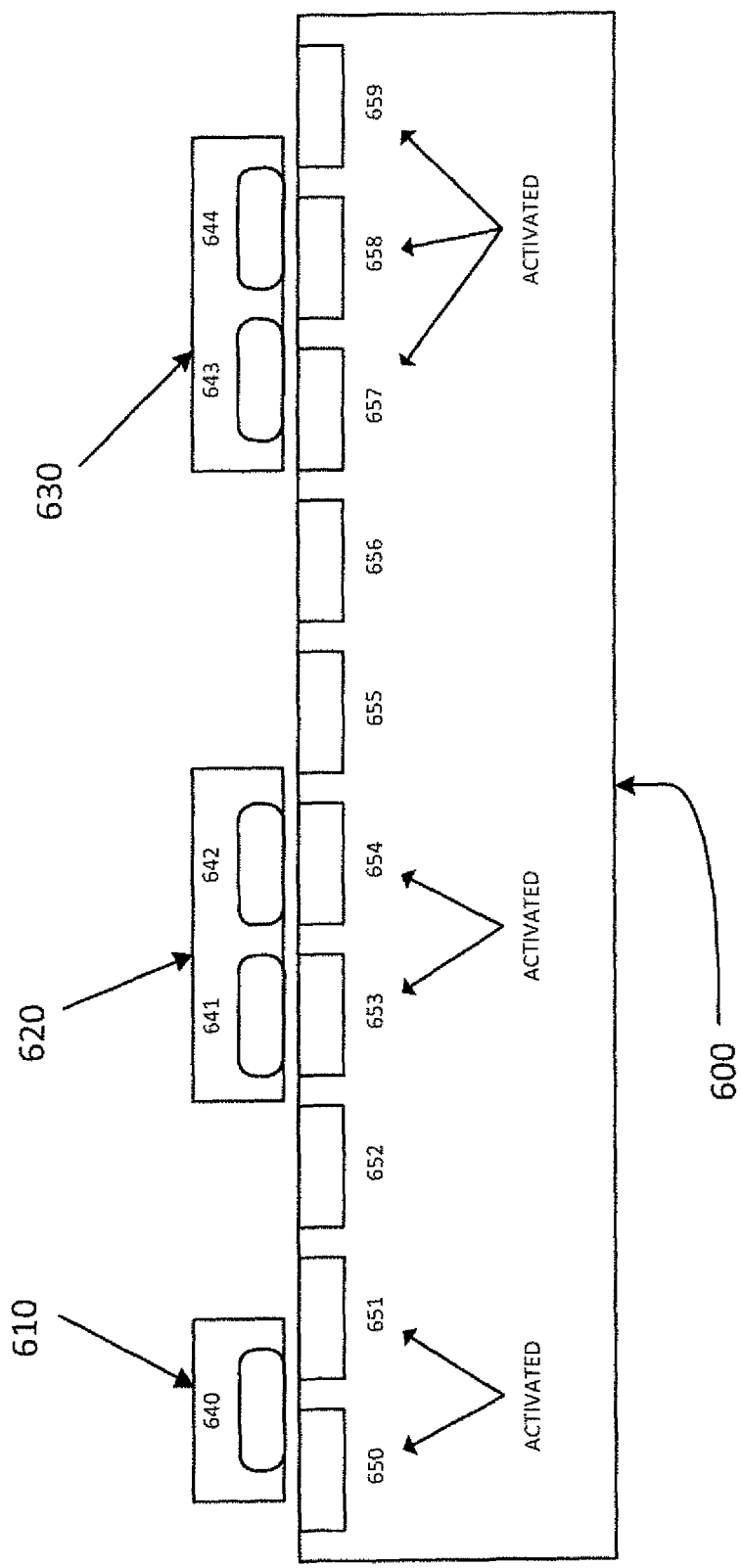
Figure 7:
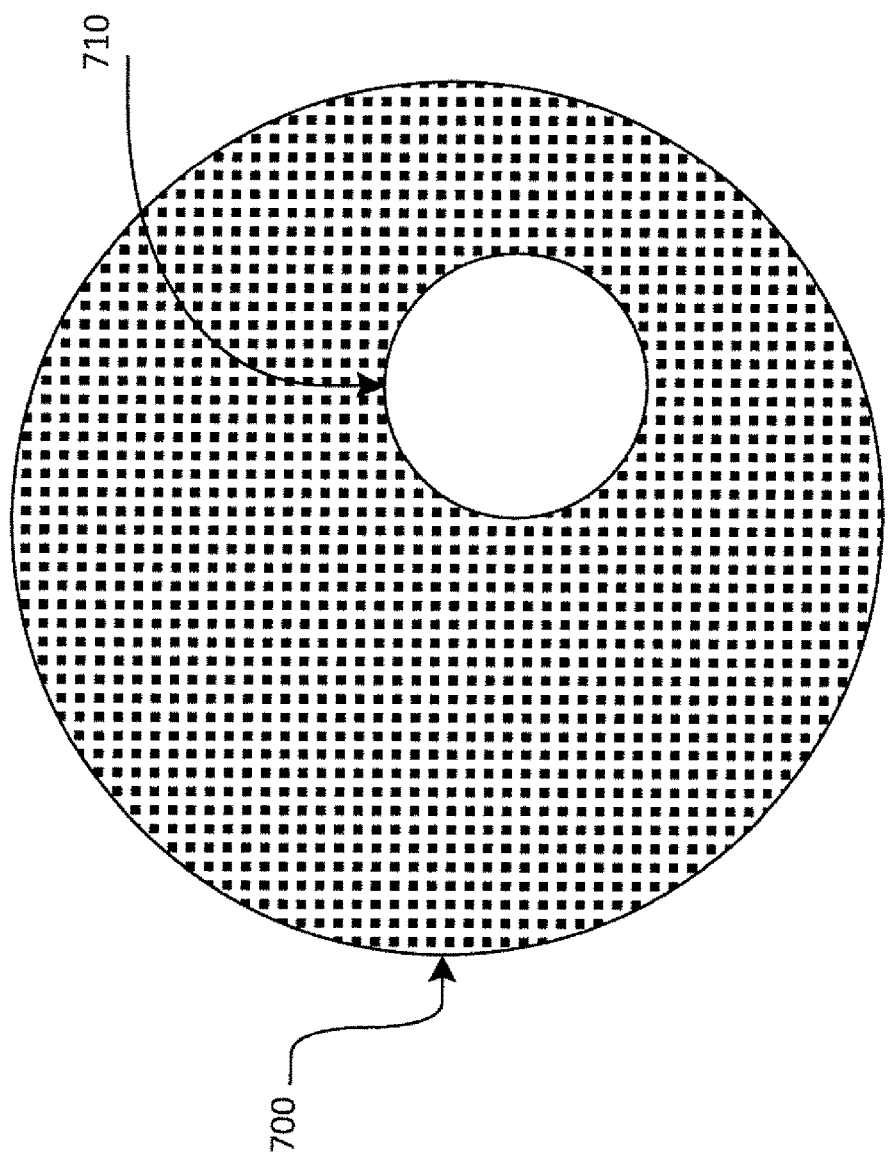
Figure 8:
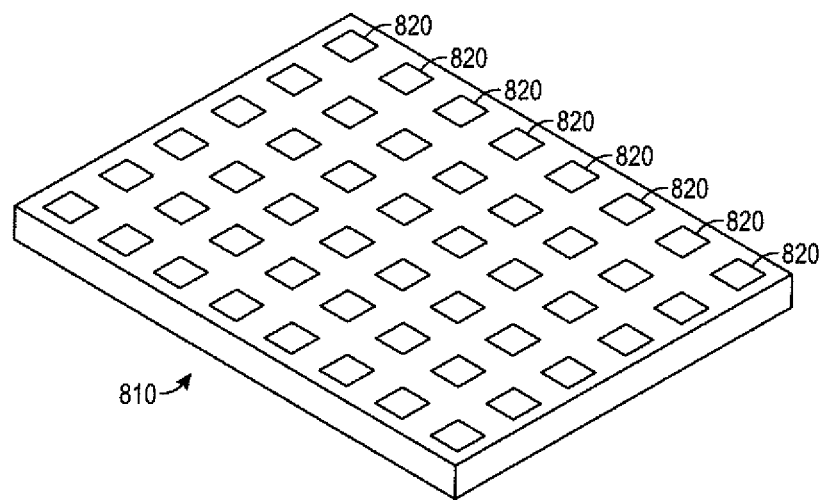
Figure 9:
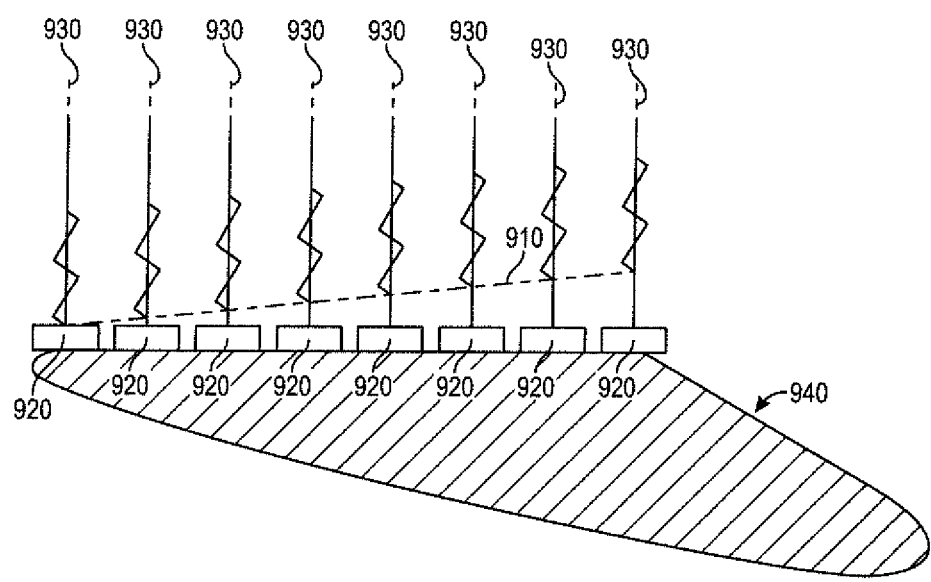
Figure 10:
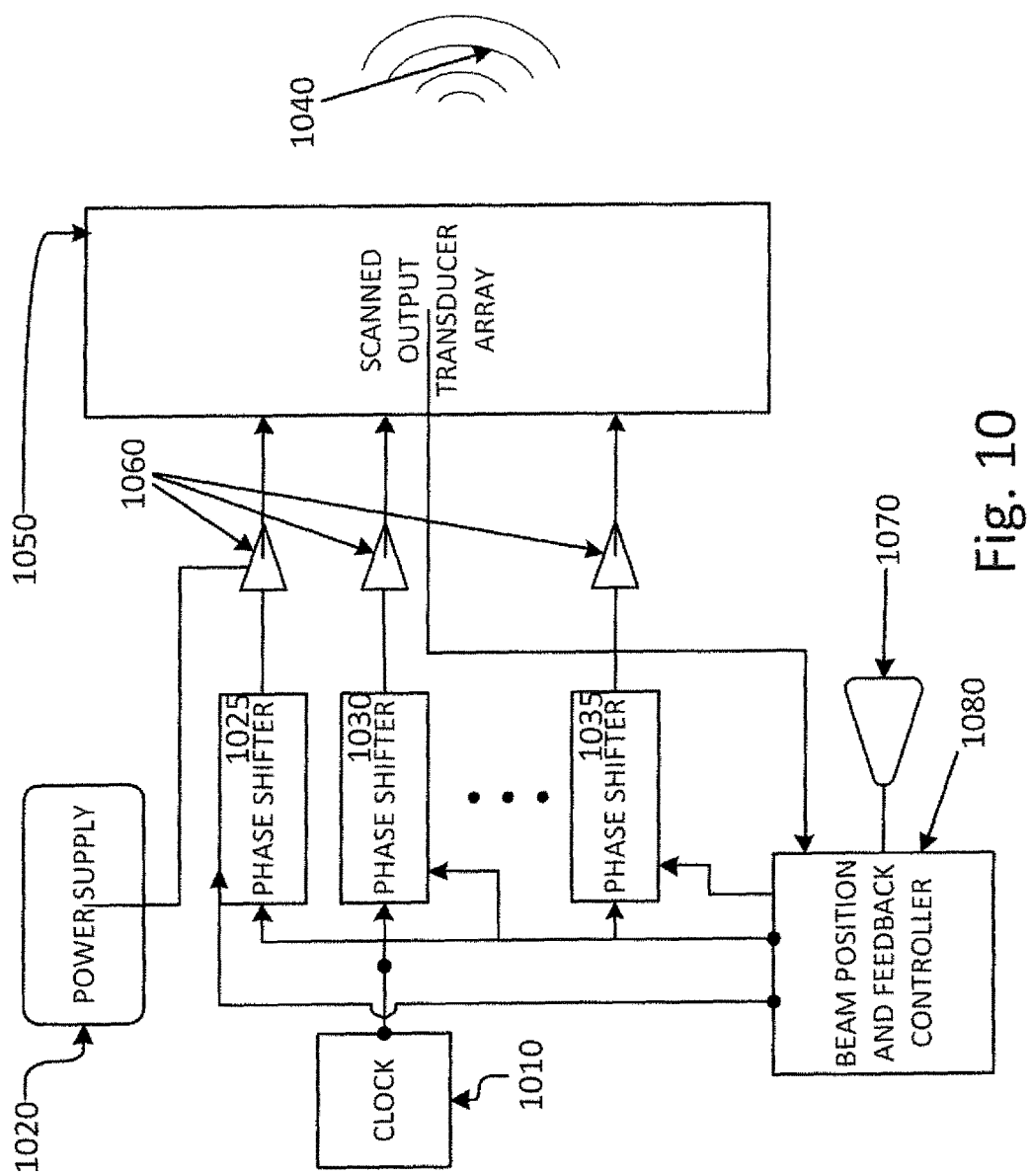
Figure 11:
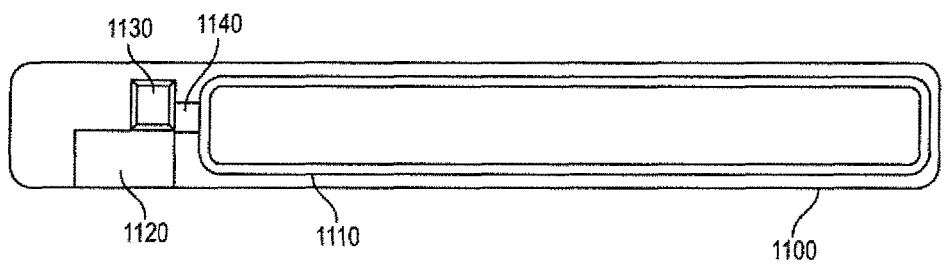
Figure 12:
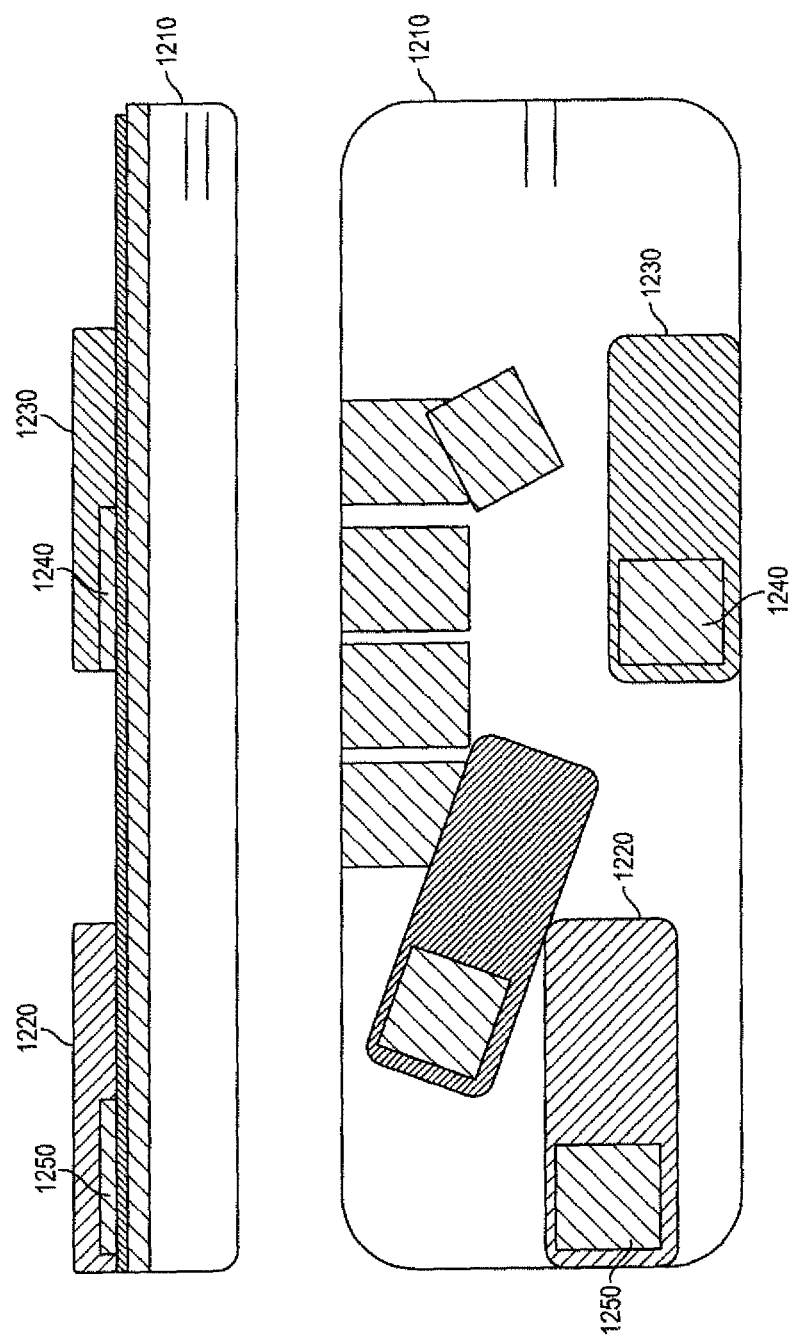
Figure 13:
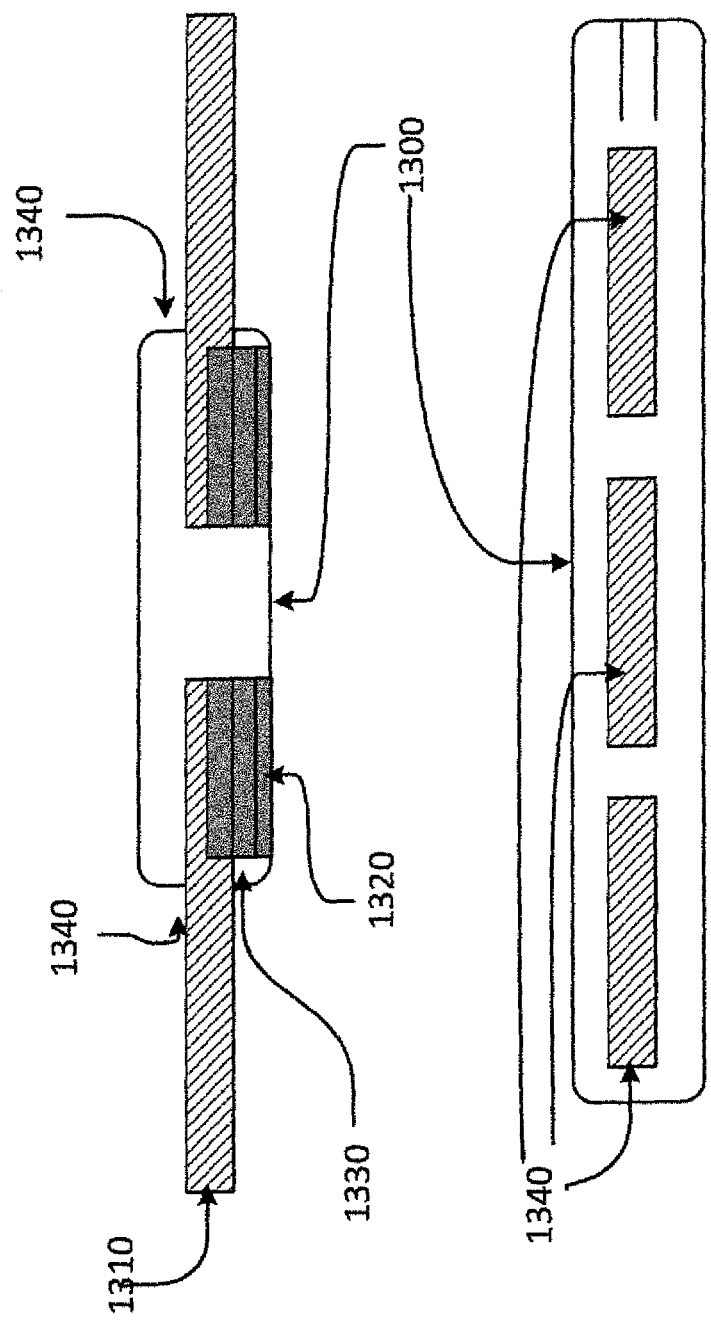
Figure 14:
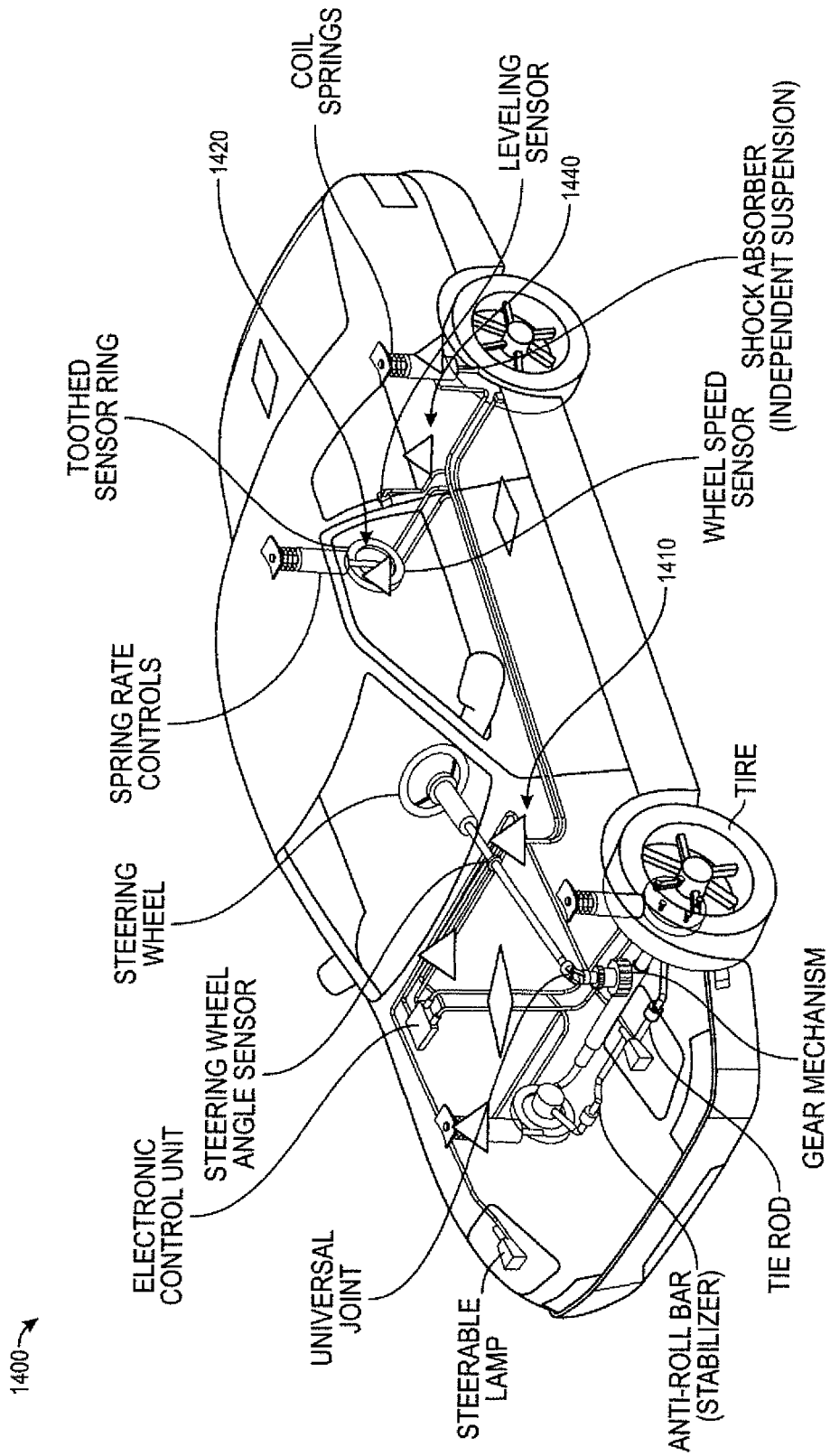
Figure 15:
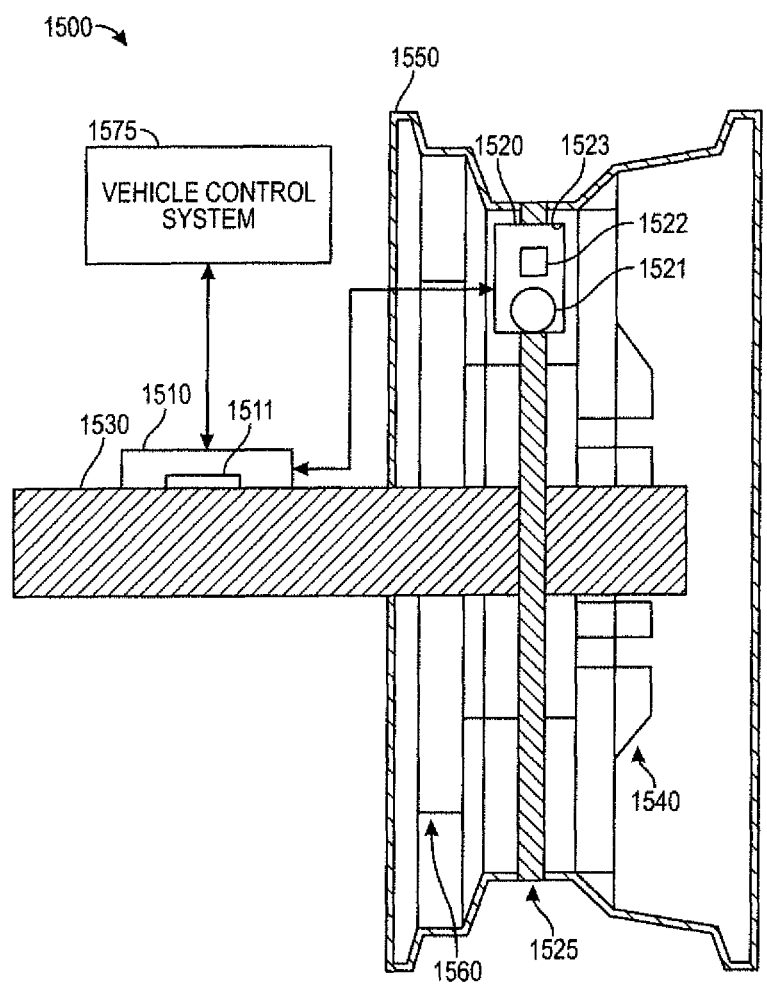
Figure 16:
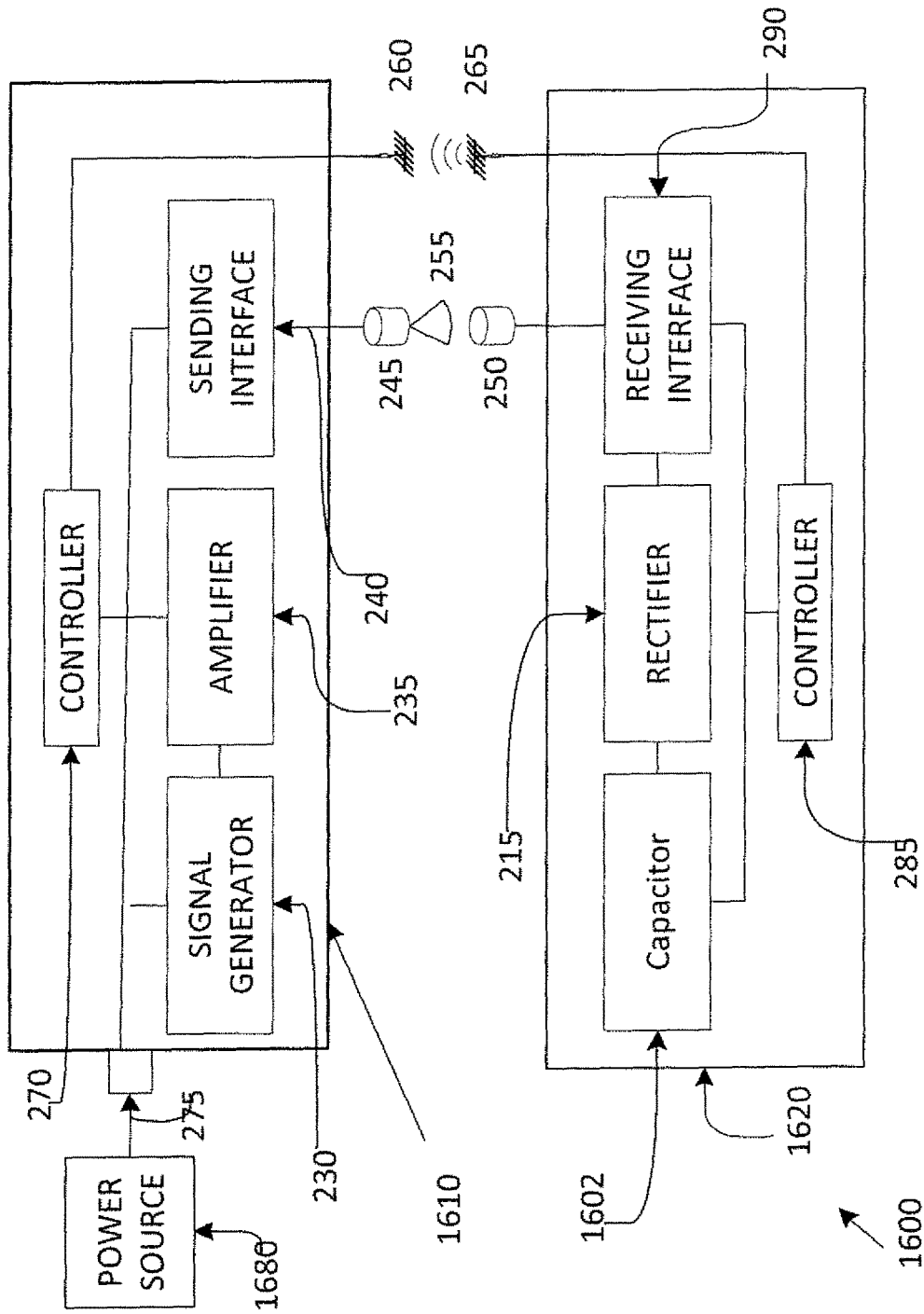
Figure 17:
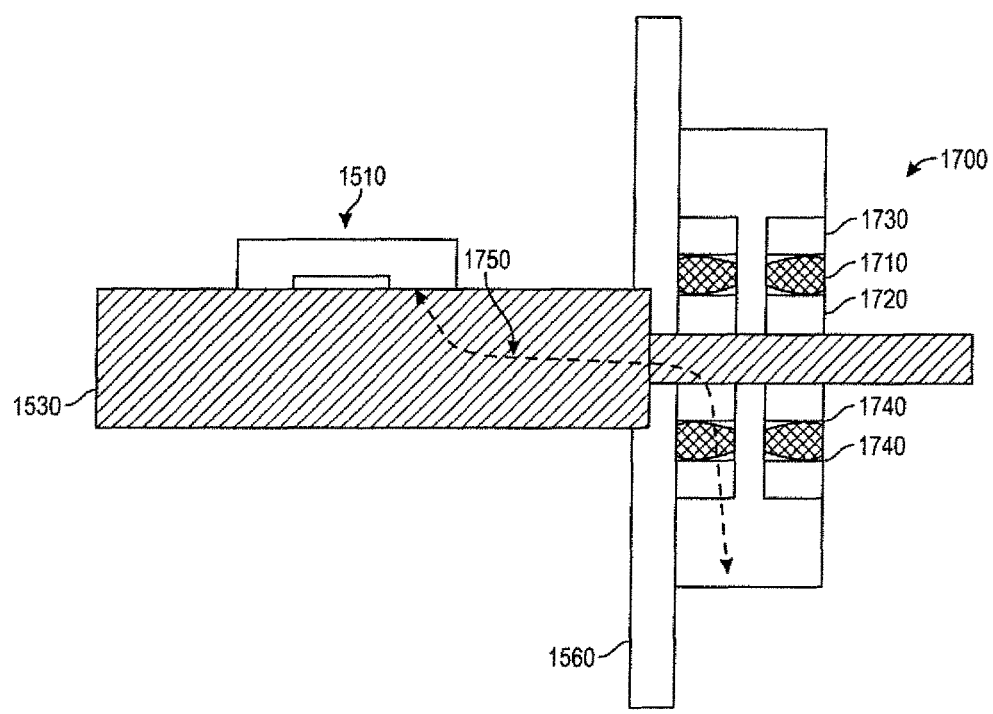
Figure 18:
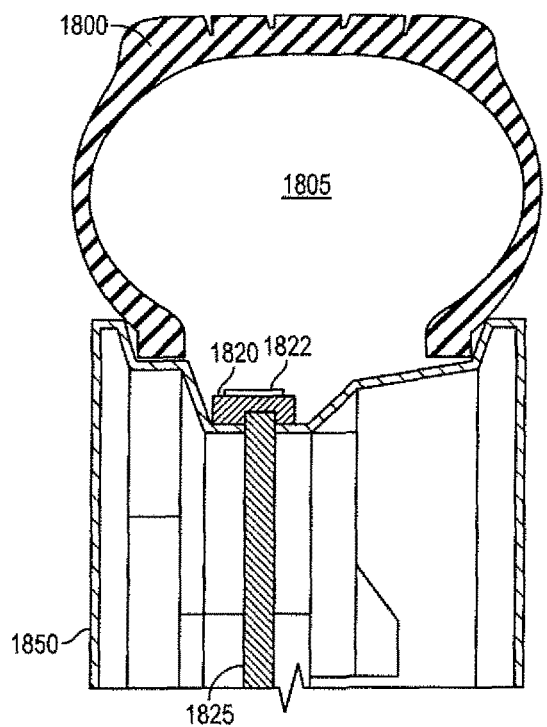
Figure 19:
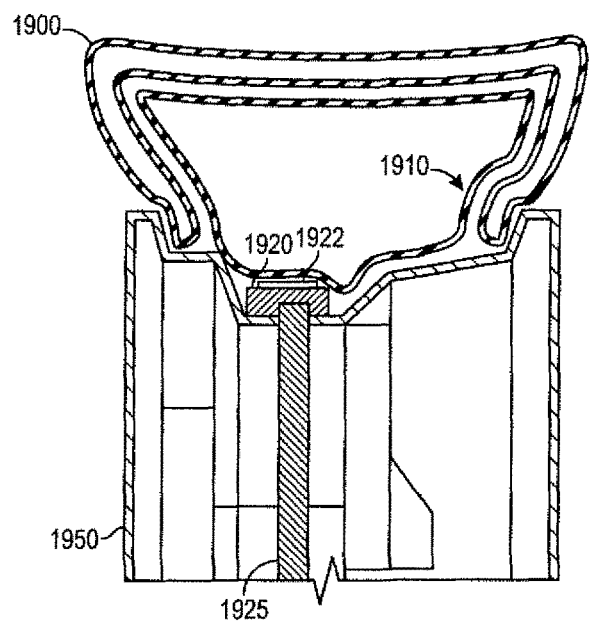
Figure 20:
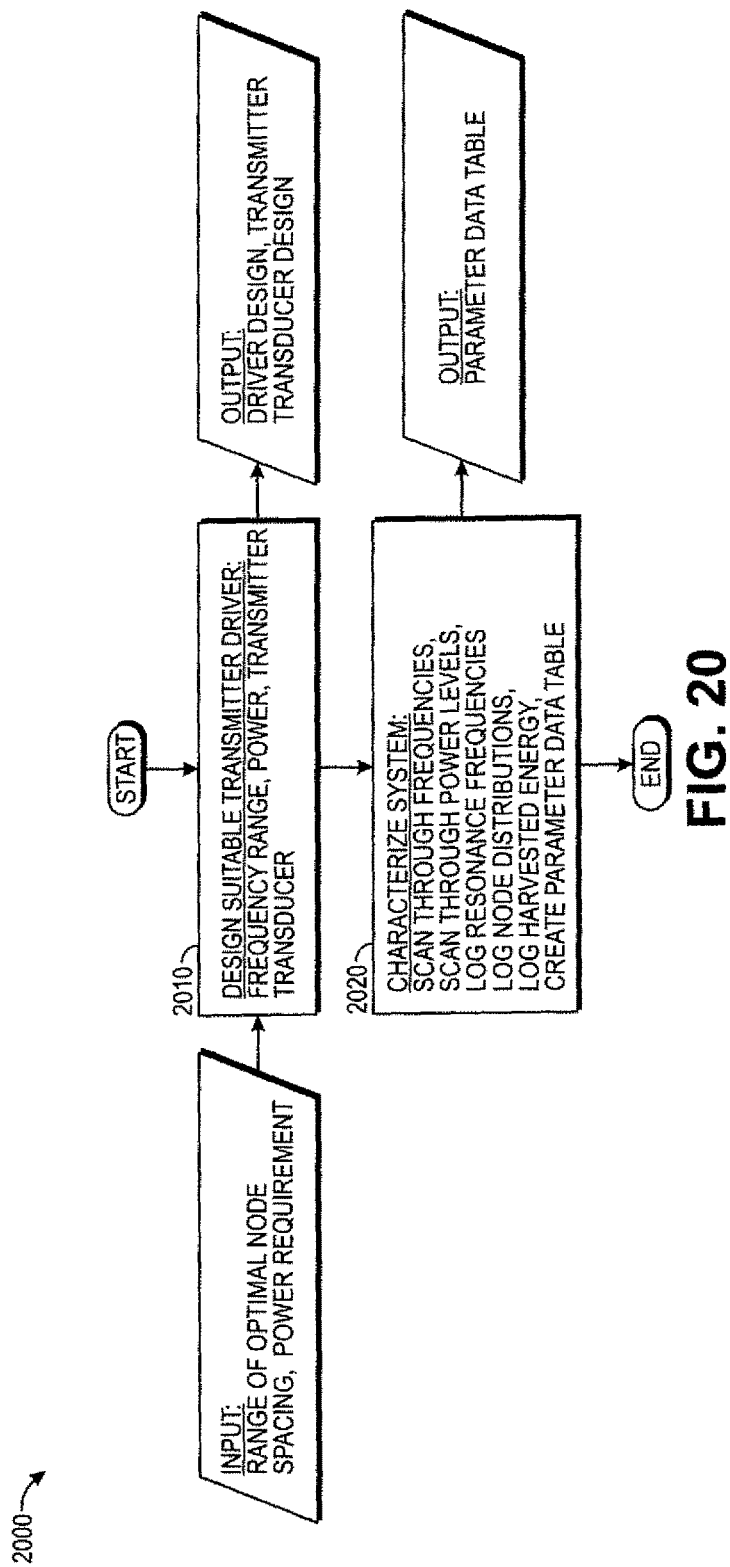
Figure 21:
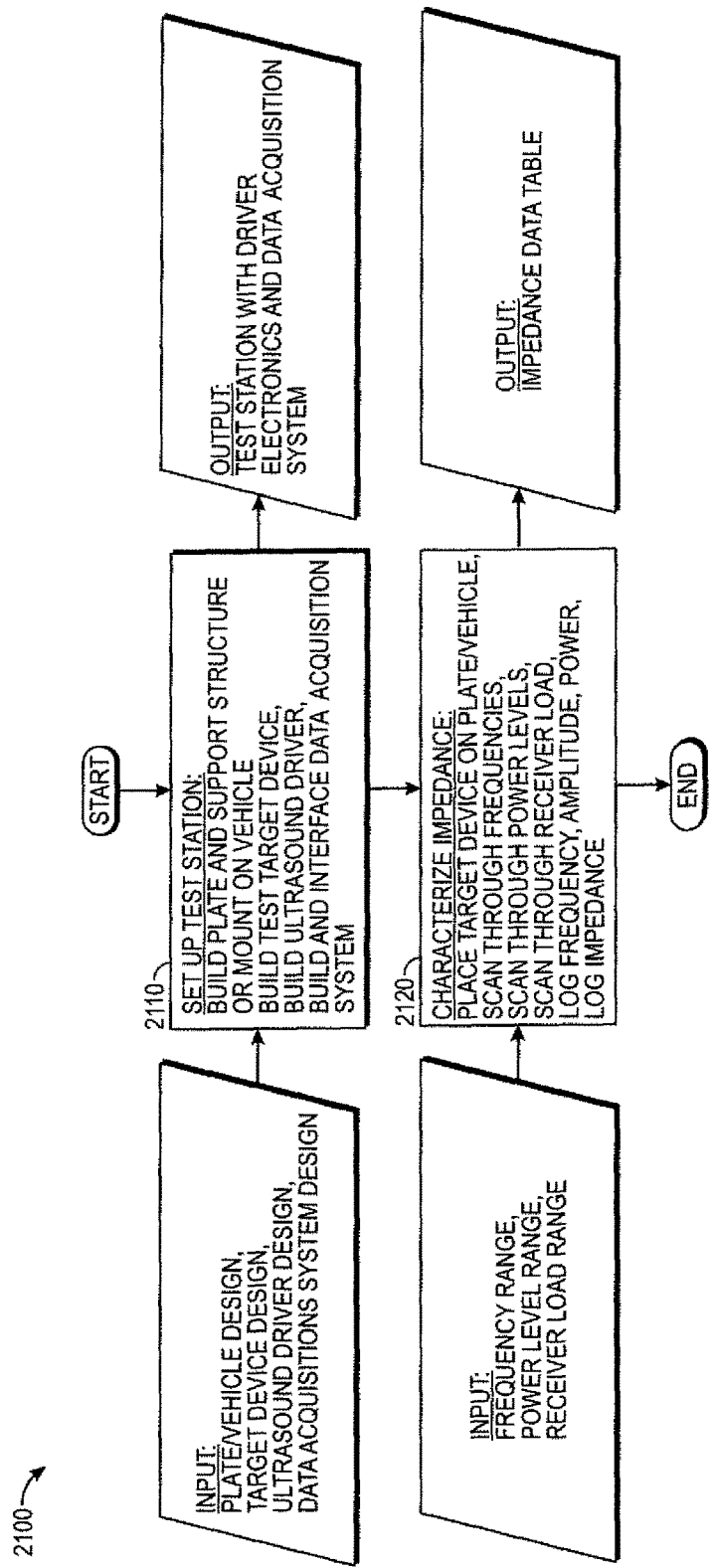
Figure 22:
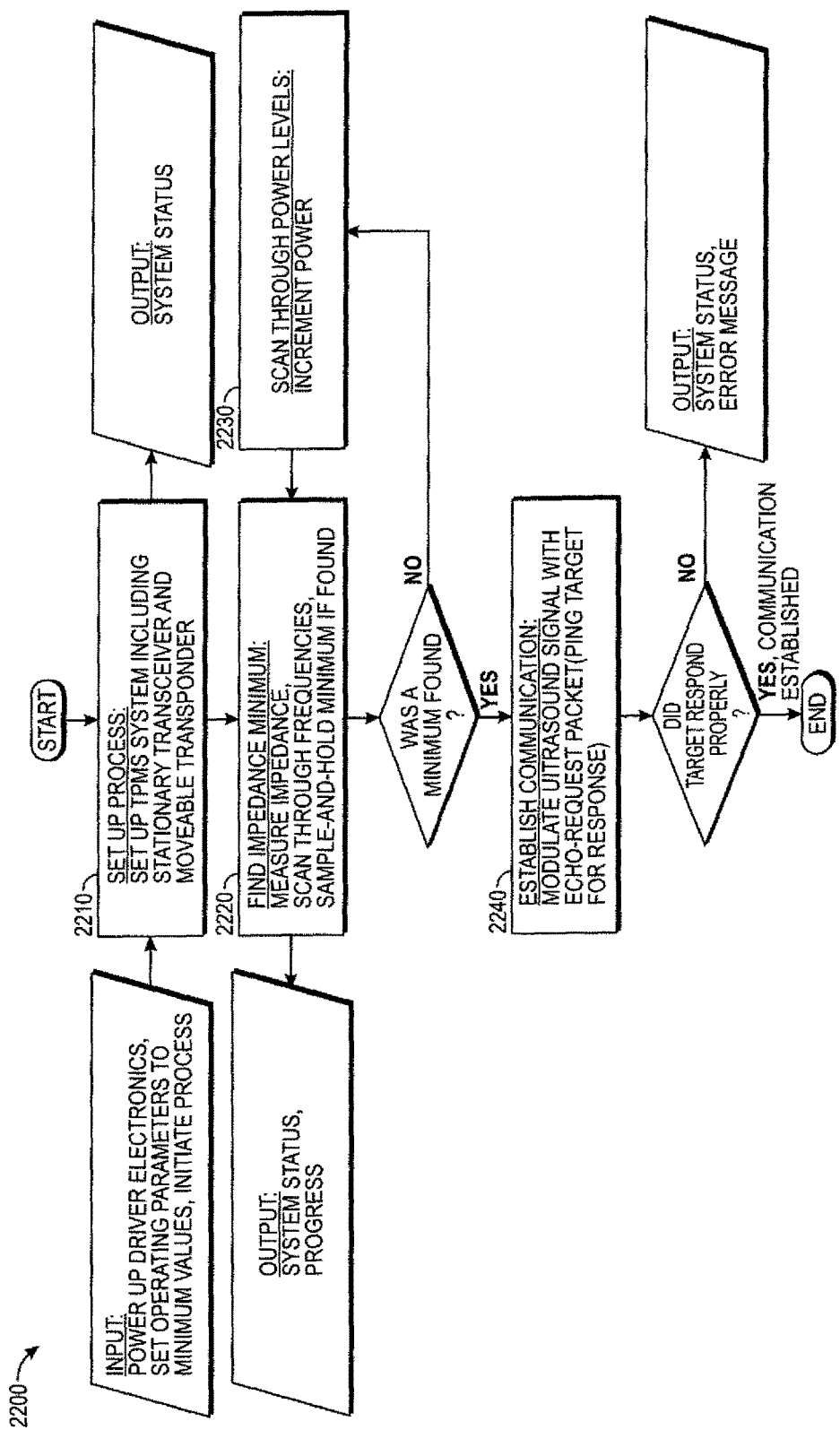
Figure 23:
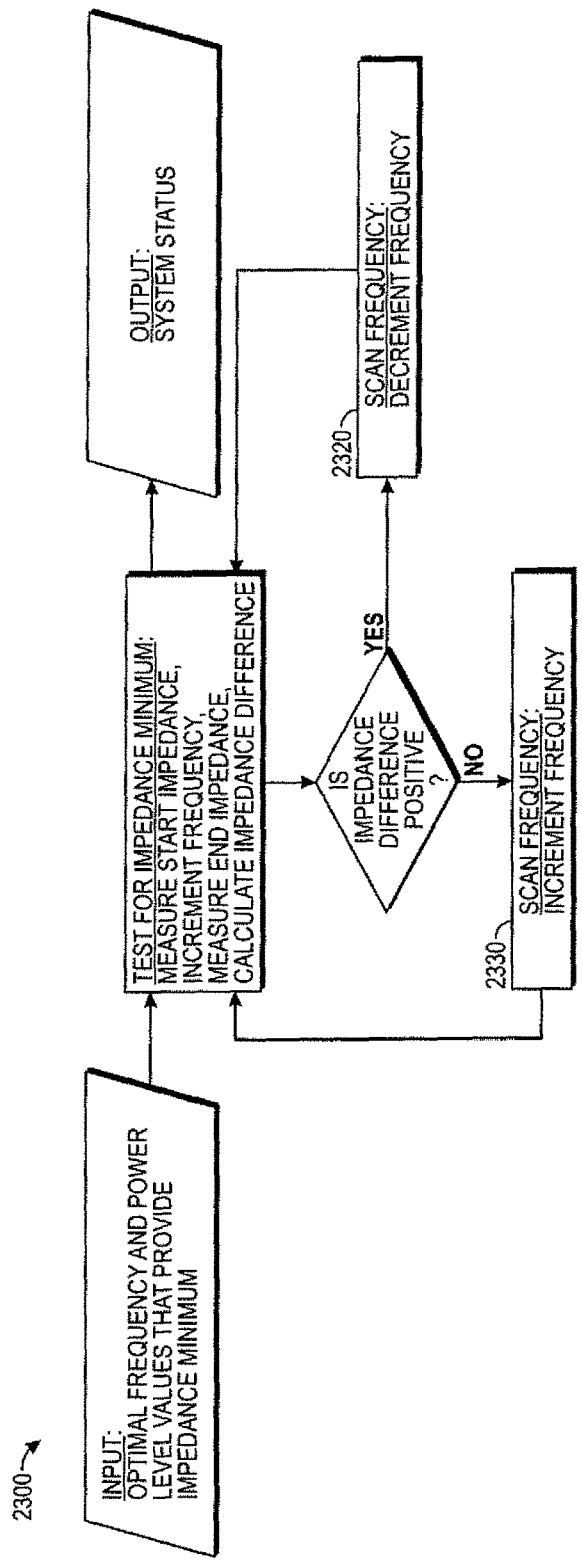
Figure 24:
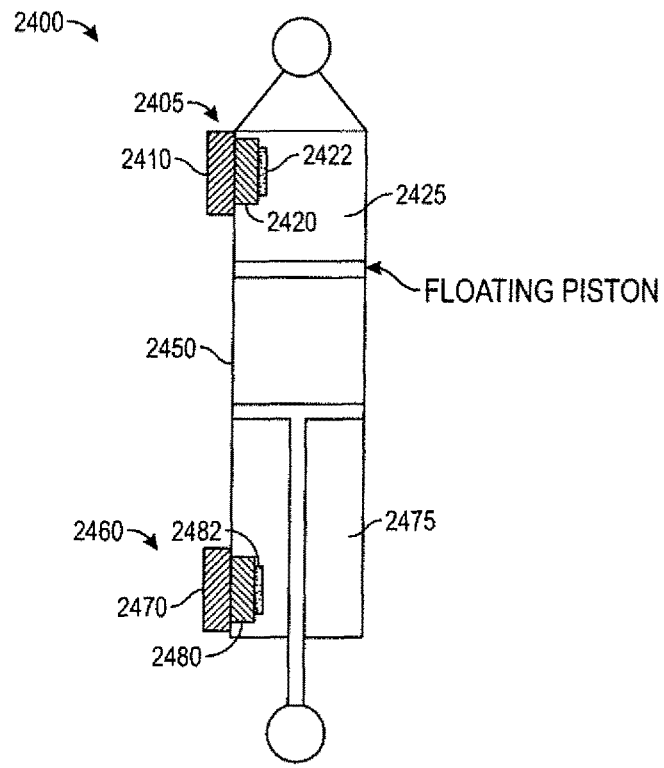
Figure 25:
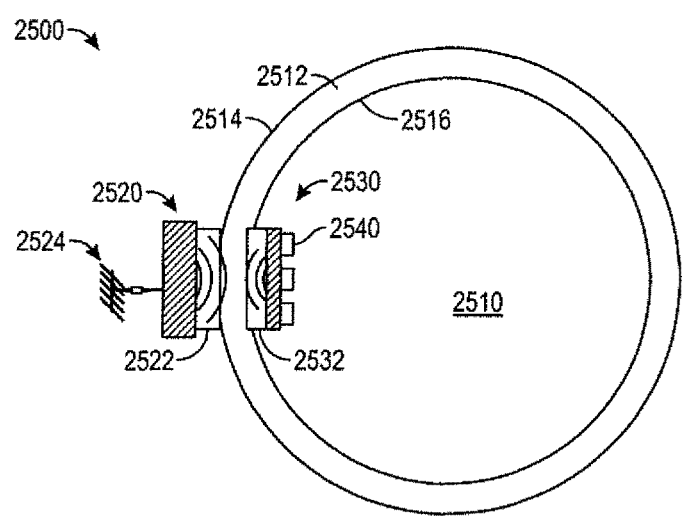
Figure 27:
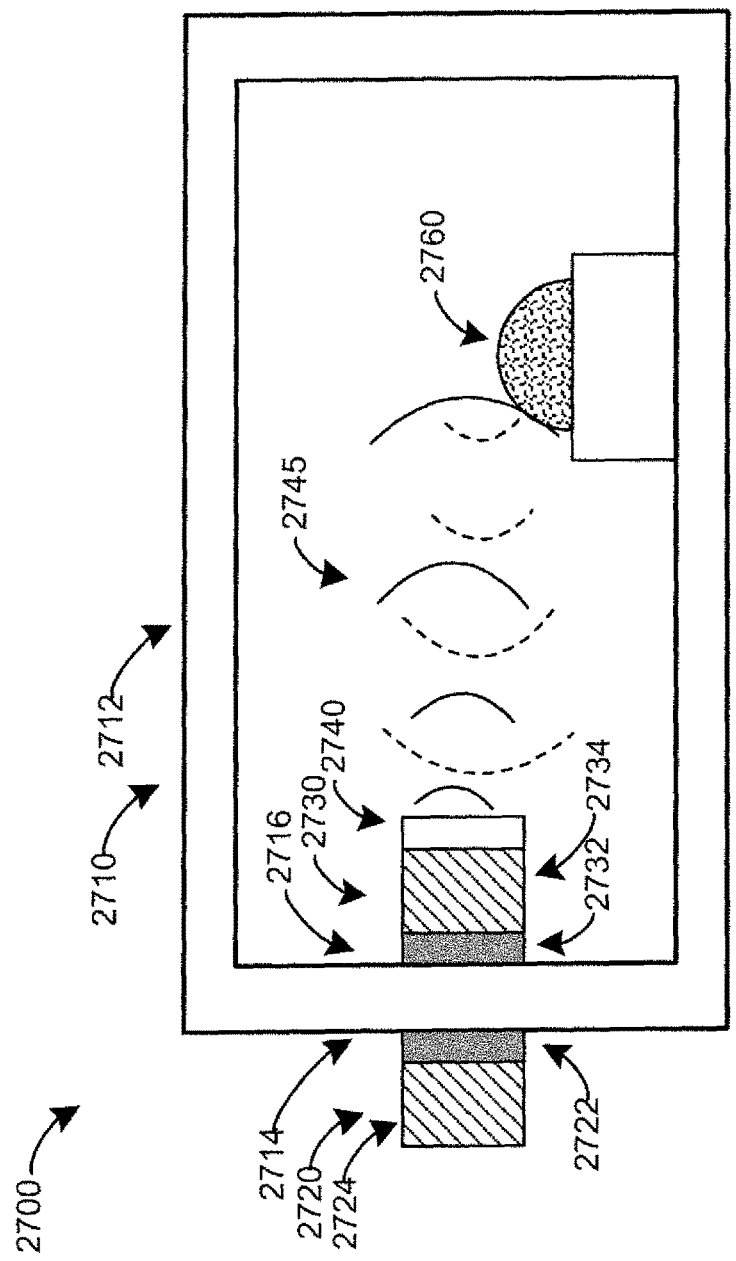
Figure 28:
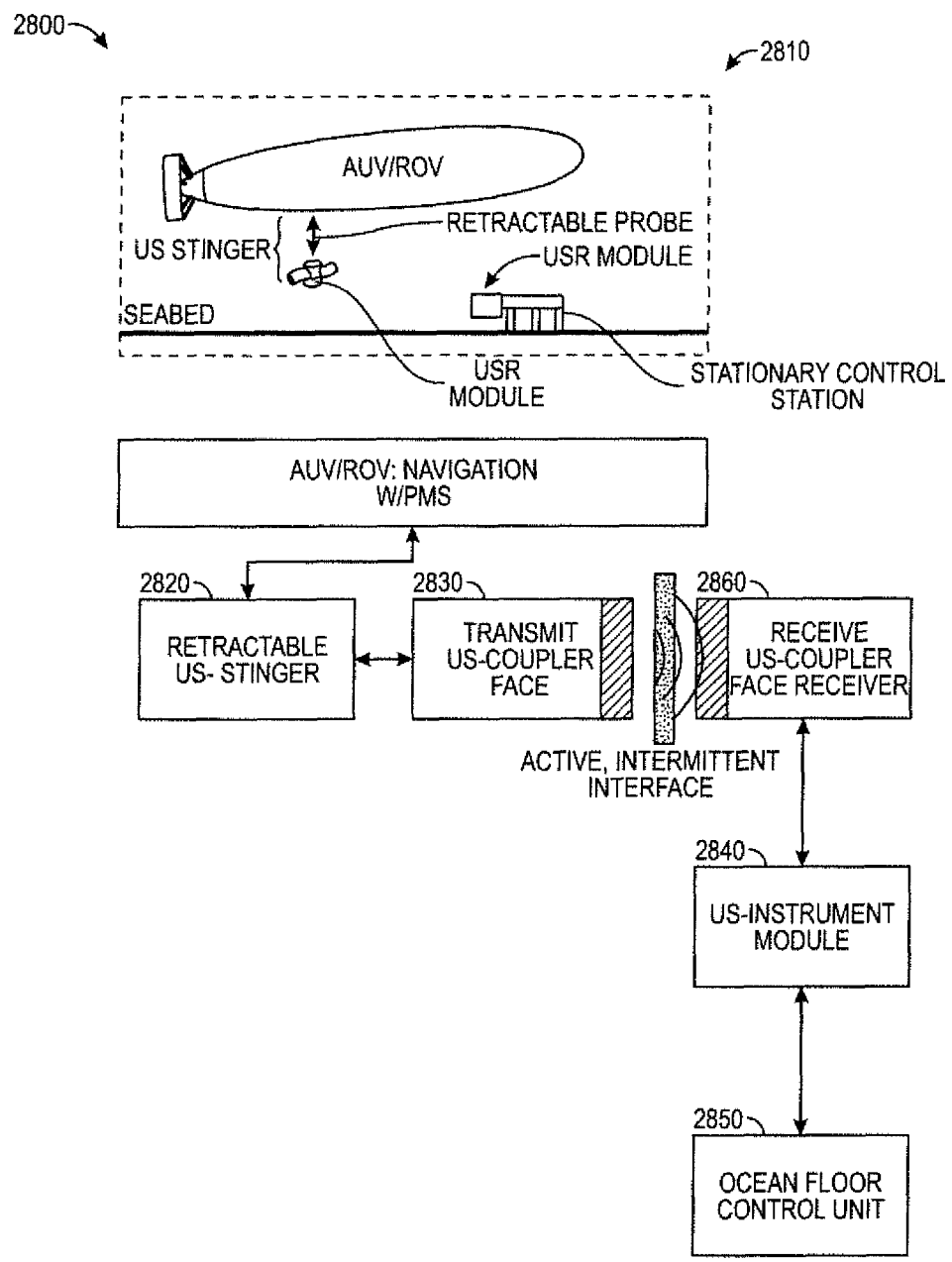
Figure 29:
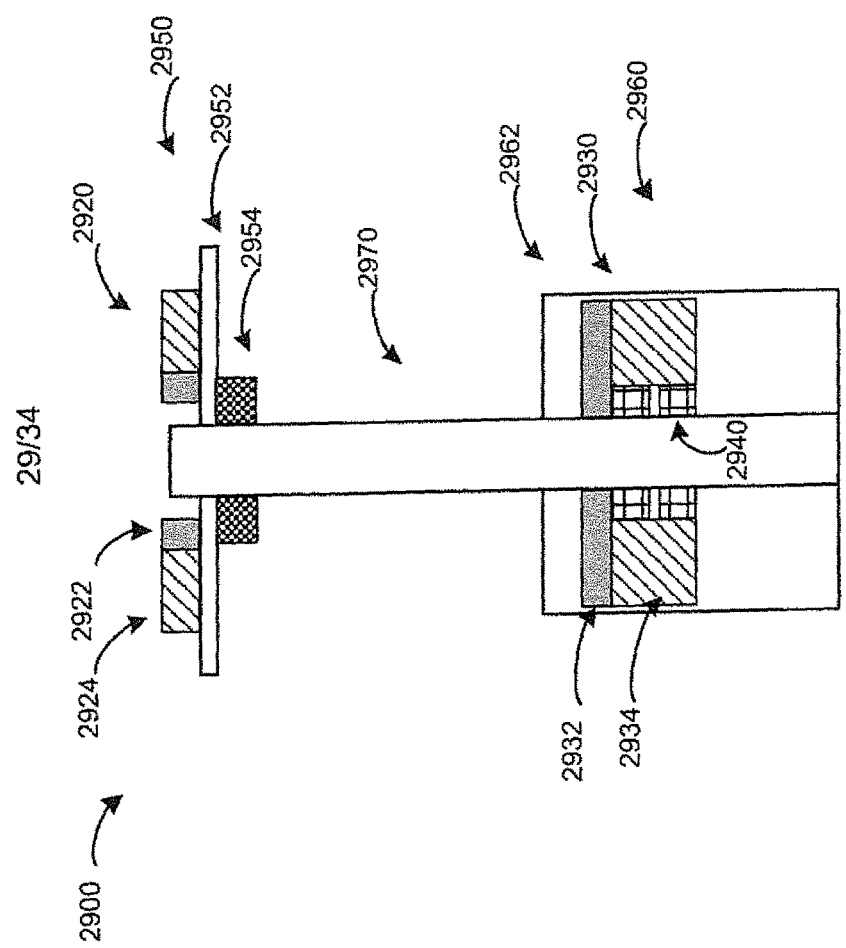
Figure 30:
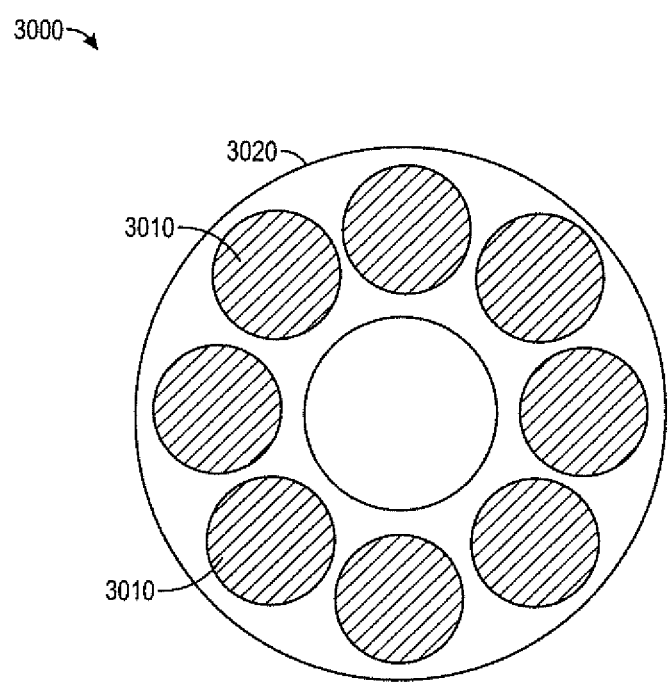
Figure 31:
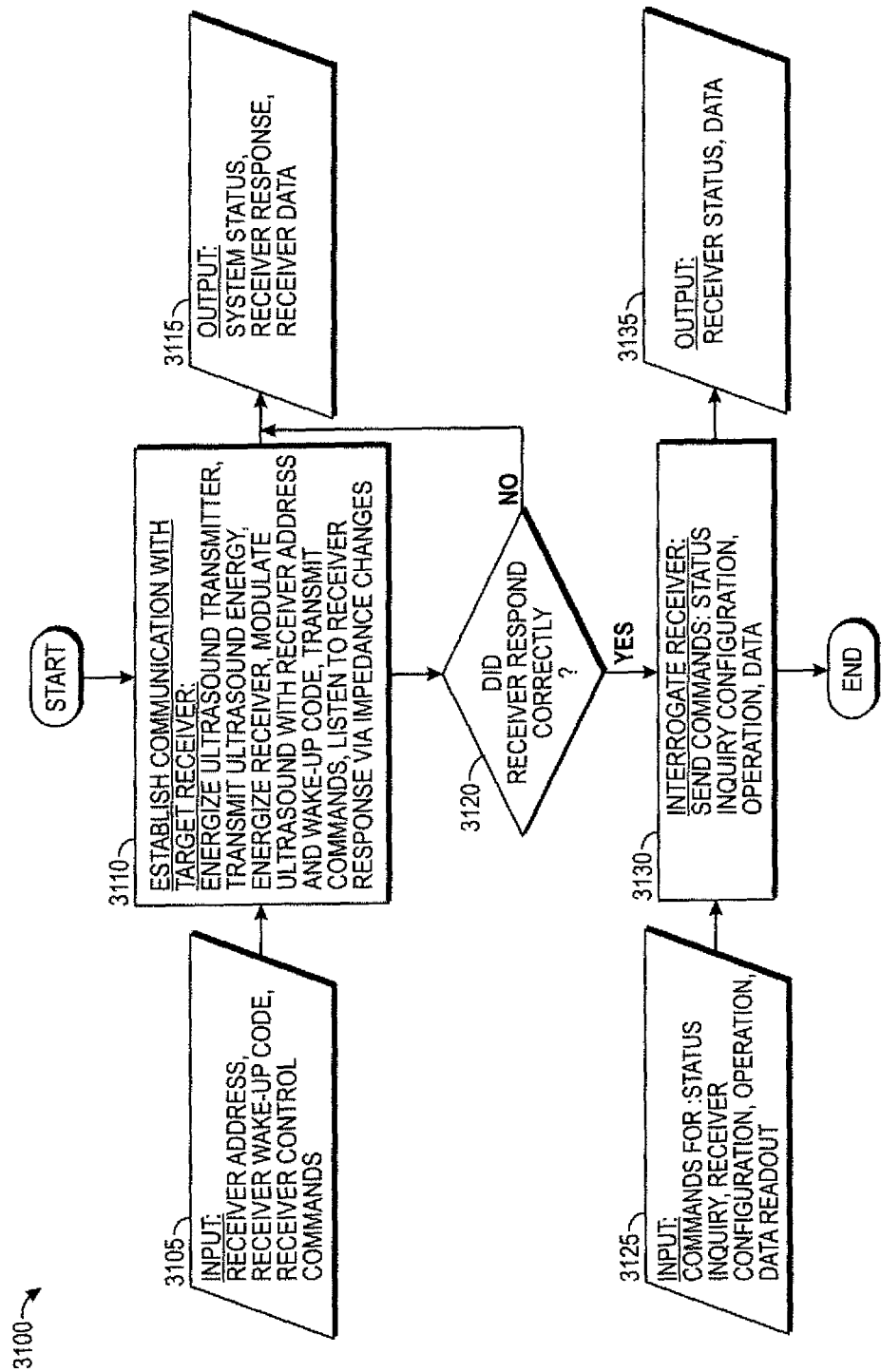
Figure 32:
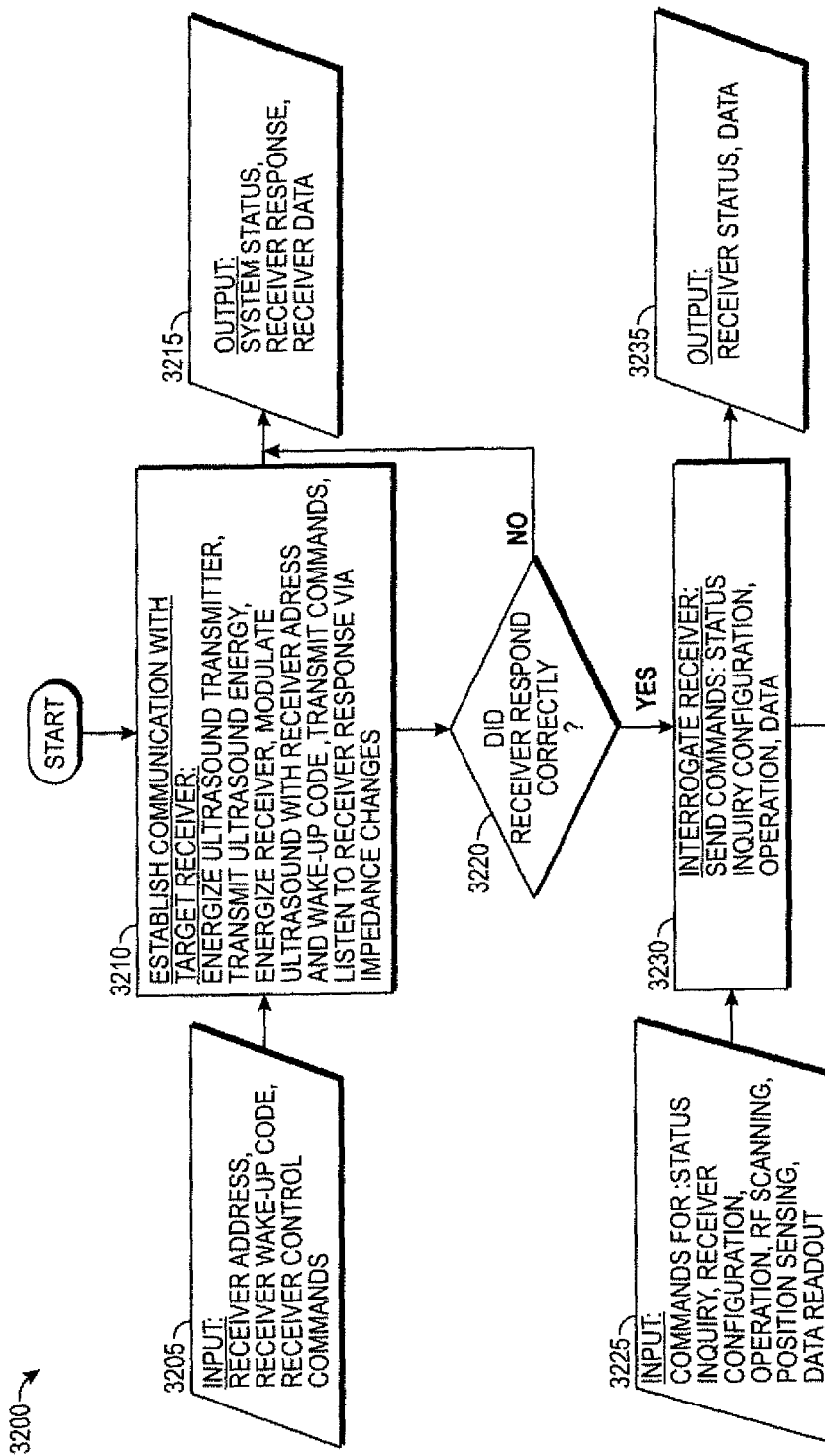
Figure 33:
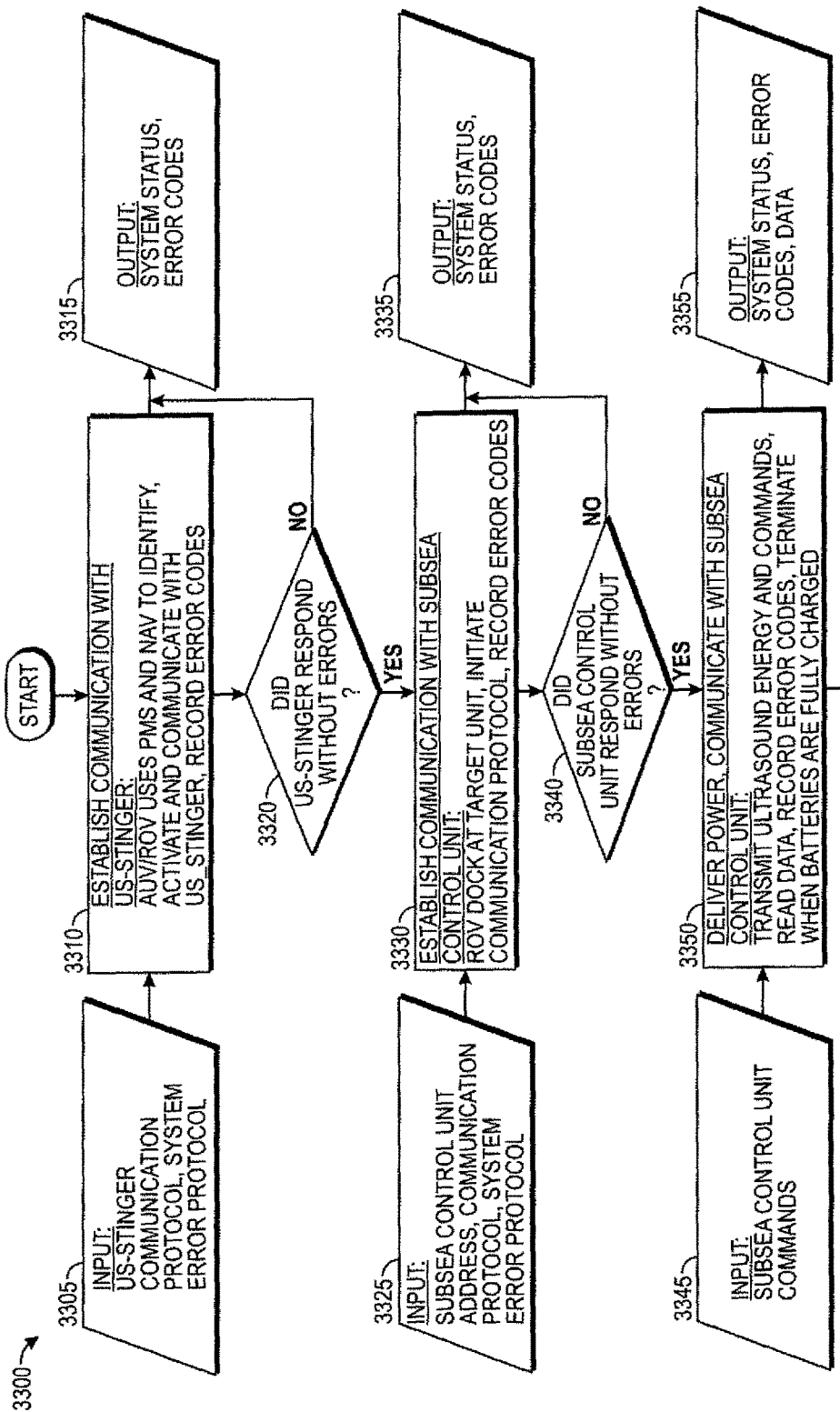
Figure 34:
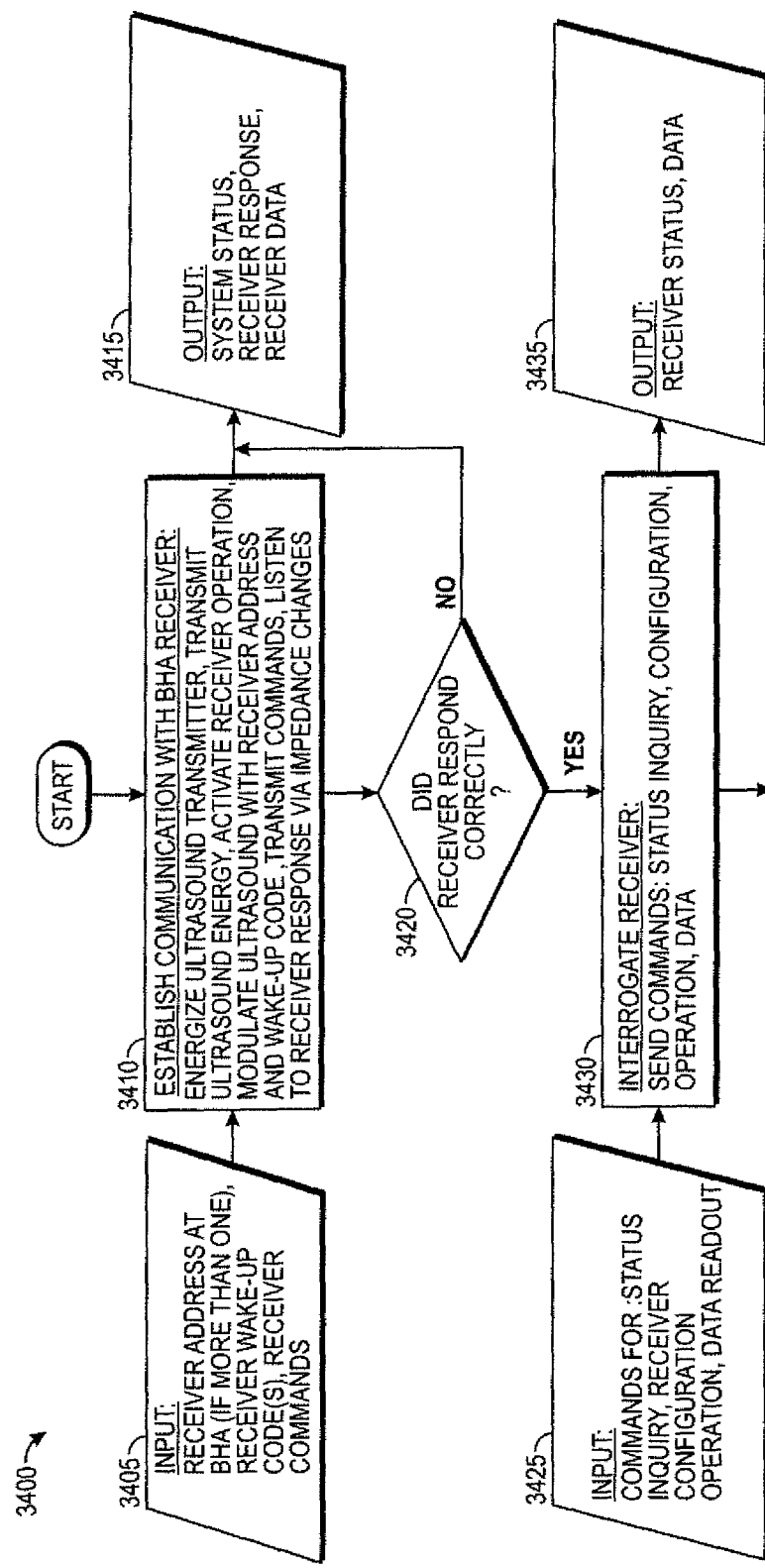
Figure 35:
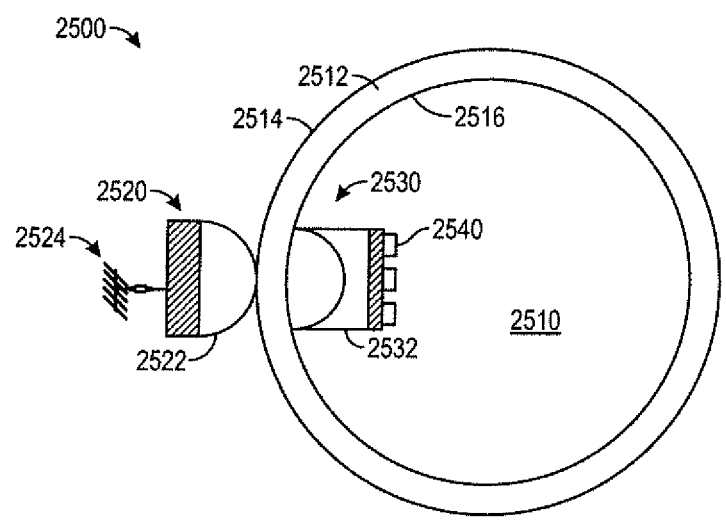

FIG. 6 demonstrates the selective activation of an exemplary transducer array of an electroacoustic charging system;

FIG. 7 is the top down view of an exemplary transducer array of an electroacoustic charging system;

FIG. 8 projects an isometric view of an exemplary two-dimensional ultrasonic transducer array of an electroacoustic power pad for the purposes of charging in a non-mechanical alignment environment;

FIG. 9 depicts an exemplary temporal abstraction of the side view of 2-dimensional electroacoustic phased array and corresponding wavefront steering for non-mechanical alignment;

FIG. 10 illustrates an abstraction circuit used to produce electrical signals delivered to 2-dimensional electroacoustic phased arrays;

FIG. 11 illustrates the side view of an exemplary electroacoustic charging cover circumscribing a generic portable device;

FIG. 12 depicts top and side views of an exemplary electroacoustic charging system comprising electroacoustic power pad and portable devices;

FIG. 13 depicts top and side views of an exemplary electroacoustic charging system comprising electroacoustic power pad and portable devices according to an alternate embodiment;

FIG. 14 illustrates in-situ autonomous sensor charging of an electroacoustic system in a modern automobile according to an additional embodiment of the present invention;

FIG. 15 illustrates a cutaway and diagrammatic view of a rim and axle that includes a direct tire pressure monitoring system (DTPMS) that includes one or more ultrasonic transducer components according to one or more embodiments;

FIG. 16 illustrates a block abstraction of an electroacoustic DTPMS comprising a stationary transceiver and a movable transponder according to one or more embodiments;

FIG. 17 illustrates a detailed cutaway of the non-rotating member of the suspension system (axle) and rotating break rotor to illustrate the path of ultrasound energy between the stationary transceiver and the movable transponder, according to one or more embodiments;

FIG. 18 illustrates a movable transponder that includes a pressure sensor for measuring the air pressure of a tubeless tire according to one or more embodiments;

FIG. 19 illustrates a movable transponder that includes a pressure sensor for measuring the air pressure of a tubed tire according to one or more embodiments;

FIG. 20 is a flow chart for designing a testing apparatus and transmitter driver and mapping the parameter field of a DTPMS according to one or more embodiments;

FIG. 21 is a flow chart for designing a testing station and transmitter driver and mapping the parameter field of the stationary transceiver according to one or more embodiments;

FIG. 22 is a flow chart for optimizing the ultrasound energy transfer from the stationary transceiver to the movable transponder according to one or more embodiments;

FIG. 23 is a flow chart for dynamically optimizing the ultrasound energy transfer from the stationary transceiver to the movable transponder while the movable transponder is in motion according to one or more embodiments;

FIG. 24 is a cutaway and diagrammatic view of a shock absorber of a vehicle suspension system that includes one or more sensors coupled to ultrasonic transducer components according to one or more embodiments;

FIG. 25 is a cross section of a system for providing ultrasonic energy and converted electrical power to a sensor in a metallic pipe according to one or more embodiments;

FIG. 26A is a cross section of a system for providing ultrasonic energy and converted electrical power to a sensor in a vessel having a metallic wall;

FIGS. 26B and 26C are detailed views of the ultrasound transceiver and the receiver transponder, respectively, illustrated in FIG. 26A;

FIG. 27 is a cross section of a system for providing ultrasonic energy and converted electrical power to a sensor in an enclosure or housing having a metallic wall;

FIG. 28 is a block diagram of a system for recharging a battery for an ultrasonic transponder disposed in a body of water;

FIG. 29 is a diagrammatic cross-sectional view of a system for providing ultrasonic energy and converted electrical power to a sensor along a drill string coupled to a Kelly drive;

FIG. 30 is a top view of a transducer array that can be used in the system of FIG. 29;

FIG. 31 is a flow chart for providing ultrasonic energy and converted electrical power to a sensor in a metallic pipe or in a metallic vessel;

FIG. 32 is a flow chart for providing ultrasonic energy and converted electrical power to a sensor in a metallic enclosure;

FIG. 33 is a flow chart for recharging a battery for an ultrasonic transponder disposed in a body of water;

FIG. 34 is a flow chart for providing ultrasonic energy and converted electrical power to a sensor (e.g., in a BHA) along a drill string coupled to a Kelly; and FIG. 35 is a cross section of a system for providing ultrasonic energy and converted electrical power to a sensor in a metallic pipe where the system includes electroacoustic transmitting elements disposed in a convex configuration and electroacoustic receiving elements disposed in a concave configuration, according to one or more embodiments.

DETAILED DESCRIPTION

Aspects of this application are directed to the transmission of electrical power between electronic devices without the use of wires. More specifically, some aspects of this application pertain to the transmission of electrical power between a charging pad and electronic devices using ultrasound to overcome the aforementioned limitations enumerated in the background. One or more embodiments or implementations are hereinafter described in conjunction with the drawings, where like reference numerals are used to refer to like elements throughout, and where the various features are not necessarily drawn to scale.

Other aspects hereof are directed to a novel electroacoustic charging system of portable devices. However, it is not beyond the scope of the present invention to apply ultrasound recharging or direct power to many small consumer appliances where suitable. These include ultrasonic toothbrushes, battery powered hearing aids, and a variety of electronic devices such as cell phones, pads, and notebook computers. In the communication data device field, the present concepts can be applied to receivers, transmitters, transceivers, including those that are network-enabled such as Web-enabled to carry out communications of any presently known or equivalently understood format.

Another embodiment includes a portable, compact, light-weight power pack that can be placed in a conventional bag, purse, pocket or similar personal container for transporting to wherever the power delivery is needed.

Unlike electromagnetic radiation, ultrasound requires a medium for transmission, such as solids, air, gases, liquids, and liquid-laden gels. At frequencies above 100 kHz, it is significantly absorbed by air which limits the efficacy of its propagation. On the other hand, ultrasound propagation can be highly directional over short distances. Ultrasound, being a pressure wave, will not interfere with electromagnetic transmissions of nearby electronic devices in any frequency band. Ultrasound mitigates the exposure of electromagnetic radiation to the body. Although there is a dearth of research, some conjecture high intensity cell phone radiation may have negative effects on tissue of the brain. Ultrasound power transmission into tissue is reviewed by U.S. Pat. No. 8,082,041 (Radziemski), which is hereby incorporated by reference in its entirety.

Ultrasound can be used to recharge batteries or capacitors (UltraSound Electrical Recharging—USer™) or to provide power directly to a device (UltraSound Electrical Power transfer—Usep™), both of which the present application is applicable to. Convenient charging of batteries for small electronics remains problematic, particularly in the area of cell phones where quotidian use requires frequent recharging. The appearance of various charging methods on the market, including electromagnetic induction chargers from Panasonic, Qualcomm, et al. is evidence of an unmet technological need which the present invention addresses, in addition to pocket chargers such as the Halo2Cloud. Other aspects of this application are directed to a system that transmits electrical power from a first unit to a second unit using ultrasound to power a sensor coupled to the second unit. In a specific example, the foregoing system is a DTPMS. Such a system can overcome one or more of the limitations described in the background.

Figure 1:
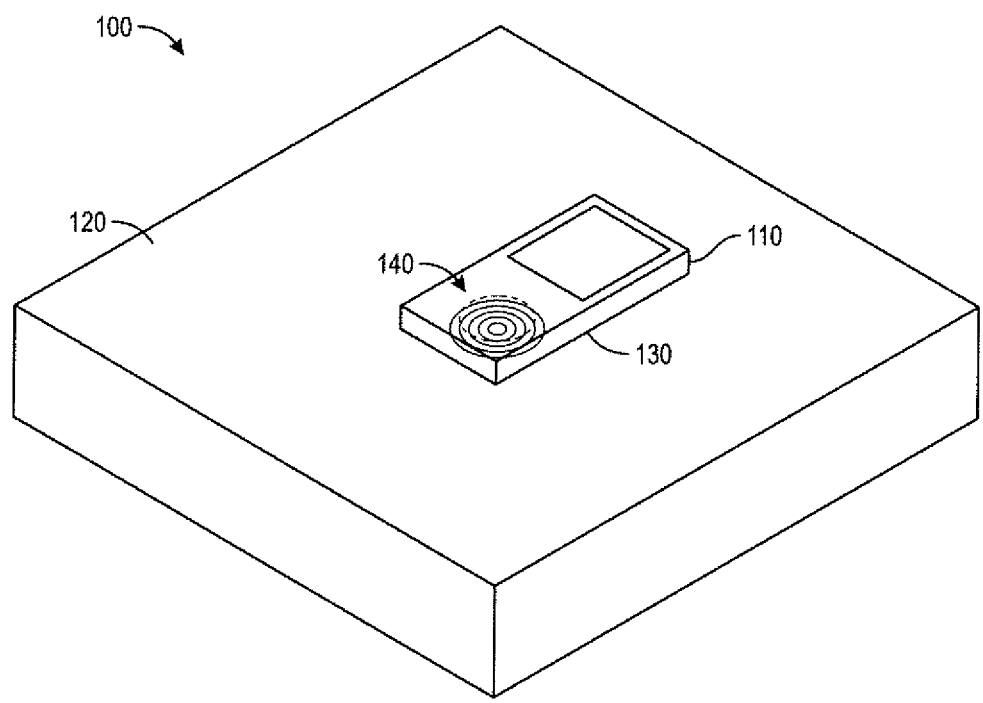
FIG. 1 illustrates an exemplary electro-acoustic power pad.

FIG. 1 illustrates an exemplary electro-acoustic power pad 100. Although only a single portable electronic device 110 is depicted, multiple devices, such as cellular telephones, are able to be charged simultaneously. The current examples are intended to be generalize beyond just cell phones, including to other mobile computing or entertainment or communication devices, etc., generally "personal data devices". Described in greater detail later in the disclosure, electroacoustic power pad comprises a charging surface 120 which mates the transmitter transducer 130 with the receiver transducer 140 which is disposed within the portable electronic device 110. The ultrasound receiver is contained within a receiver unit which may be external to portable electronic device 110 or integrated therein during fabrication of the electronic device 110.

The distance between the transmitter and receiver transducers 130, 140 may be zero (in contact) or up to 10 cm. Charging surface 120 may comprise one or more transfer media. The medium may be a liquid, solid, gas, or gel suitable for acoustic transmission. The front, flat face of the charging surface 120 may be approximately parallel to the front, flat face of the proximal to the receiver transducer 140. In another embodiment, curved faces are used to enhance focusing effects that ameliorate power transfer. In other embodiments, the distance between the transmitter and receiver transducers 130, 140 may be up to 100 cm or more, depending on the application, the ultrasound frequency, power delivered to the transmitter transducers 130 and, most importantly, acoustic medium.

Figure 2:
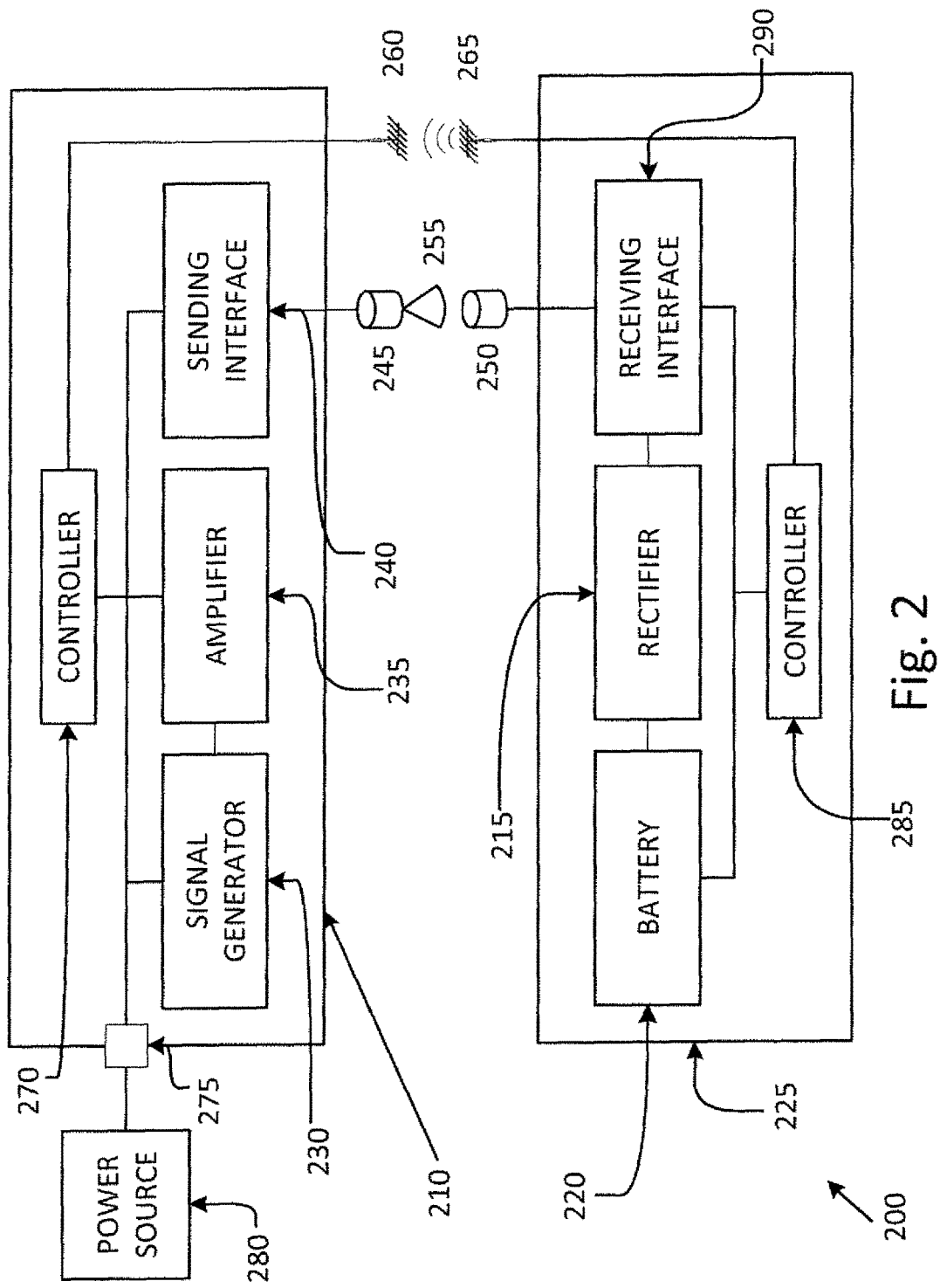
FIG. 2 depicts an exemplary abstraction of an electroacoustic charging system comprising electroacoustic power pad and portable device electroacoustic receiver.

FIG. 2 depicts an exemplary block abstraction of an electroacoustic charging system 200 comprising electroacoustic transmitter 210 and electroacoustic receiver 225. Electroacoustic transmitter 210 comprises power source 280, active power adaptor 275, transmitter controller 270, signal generator 230, amplifier 235, transmitter interface 240, transmitter transducer 245 and electromagnetic antenna 260. As will be discussed in greater detail with respect to FIG. 3, power source 280 can be direct or alternating current with active power adaptor 275 having the capacity to handle both.

Transmitter controller 270 maintains command over numerous components of electroacoustic transmitter 210 either by pre-programming or active feedback loop using user set or predetermined parameters. Transmitter controller 270 sets the output current and voltage egressing from active power adaptor 275. Transmitter controller 270 then proceeds to set the output (frequency, magnitude, phase, etc.) of signal generator 230. Signal generator 230 can a variable frequency oscillator or a synthesized signal generator or other suitable waveform generating device, such as an LC circuit.

After setting the predetermined ultrasonic frequency, transmitter controller 270 amplifies the electrical signal via amplifier 235 and transmitter interface 240. Electroacoustic power levels can be set manually by an input command or be placed under the control of a feedback loop which keeps it at the predetermined value. A useful feedback parameter, whose value is relayed from the electroacoustic receiver 225 to the transmitter controller 270, is the power received at the ultrasonic receiver transducer 250. This information is transmitted over electromagnetic communication between antennae 260, 265. Typically, it would be desirable to keep the output power stable for optimum operation of the device for the purpose of direct power. However, for battery 220 charging purposes, particularly in conjunction of modern lithium ion batteries, it is desirable to vary the power as a function of discharge.

Another important function of the transmitter controller 270 is to monitor and change the frequency of the ultrasound in order to continuously maximize and stabilize the power delivery. Typically, the range of changes due to temperature are approximately 10% of the resonant frequency. Compensation is achieved via signal generator 230 or other methods which are well known to those skilled in the art. Again, the frequency can be set manually with an input command, or can be placed under the governance of the transmitter controller 270 utilizing input the feedback loop.

A receiver module 225 comprises battery 220, rectifier 215, receiver controller 285, receiver interface 290, receiver transducer 250 and electromagnetic antenna 265. In the present embodiment, battery 220 is a lithium ion battery. However, any chemical storage battery, such as lead acid, is suitable. In other embodiments, power storing capacitors are not beyond the scope of the present invention.

In operation, receiver transducer 250 and receiver interface 290 converts ultrasonic acoustic energy 255 to electrical power. Electrical power retains the shape of the transmitted waveform of ultrasonic acoustic energy 255 and needs to be transformed via rectification so as to be useful for battery 220 charging. Rectifier 215 is an electrical device that converts alternating current (AC), which periodically reverses direction, to direct current (DC), which flows in only one direction. In one or more embodiments, rectifier 215 may comprise on or more of the following: vacuum tube diodes, mercury-arc valves, copper and selenium oxide rectifiers, semiconductor diodes, silicon-controlled rectifiers and other silicon-based semiconductor switches.

In the present embodiment, rectifier 215 also comprises voltage regulation circuitry for maintaining battery 220 voltage by receiver controller 285. Within the receiver unit 225 are components for wireless communication to electroacoustic transmitter 210. These parameters comprise the disposition of battery charge, sensor location and temperature, and the load and state of the device being charged.

Figure 3:
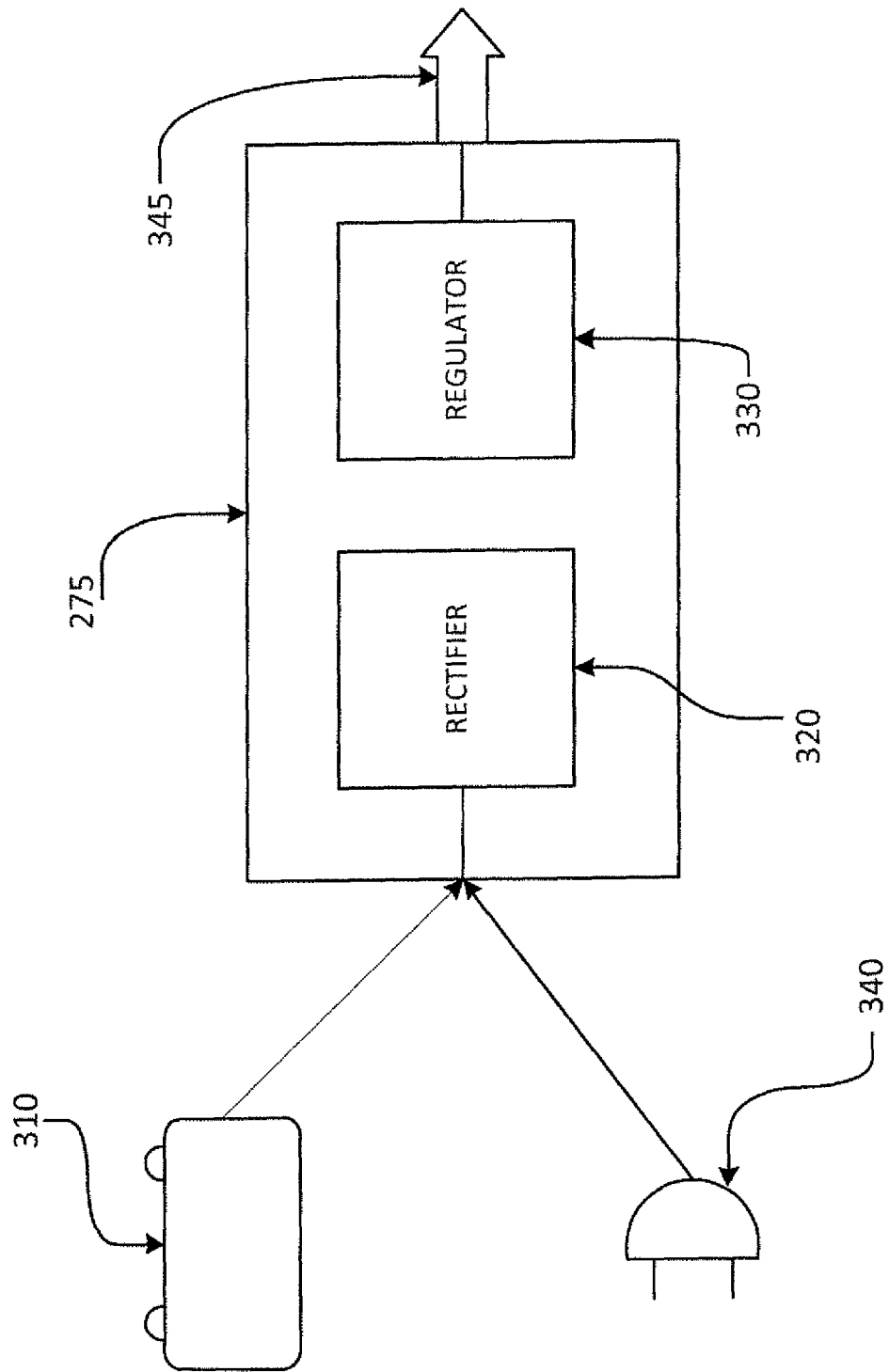
FIG. 3 illustrates an exemplary adaptive power supply to an electroacoustic charging system.

FIG. 3 illustrates an exemplary adaptive power supply 275 to an electroacoustic charging system. Adaptive power supply 275 determines whether ingressing power is derived from a DC source 310, AC source 340 or combination thereof, such as a sine wave with a DC offset. When utilizing power from DC source 310, adaptive power supply 275 converts to a voltage determined by transmitter controller 270 using a DC-DC transformer, such as, a step down, buck boost or other suitable power transistor circuitry. In one embodiment, AC source 340 is 120V, 60 Hz. AC signal is processed through rectifier 320 in accordance with prior rectification discussion. It then can either be manipulated by regulator 330 or routed through DC-DC transform circuitry, both of which achieve the same result at output 345.

Figure 4:
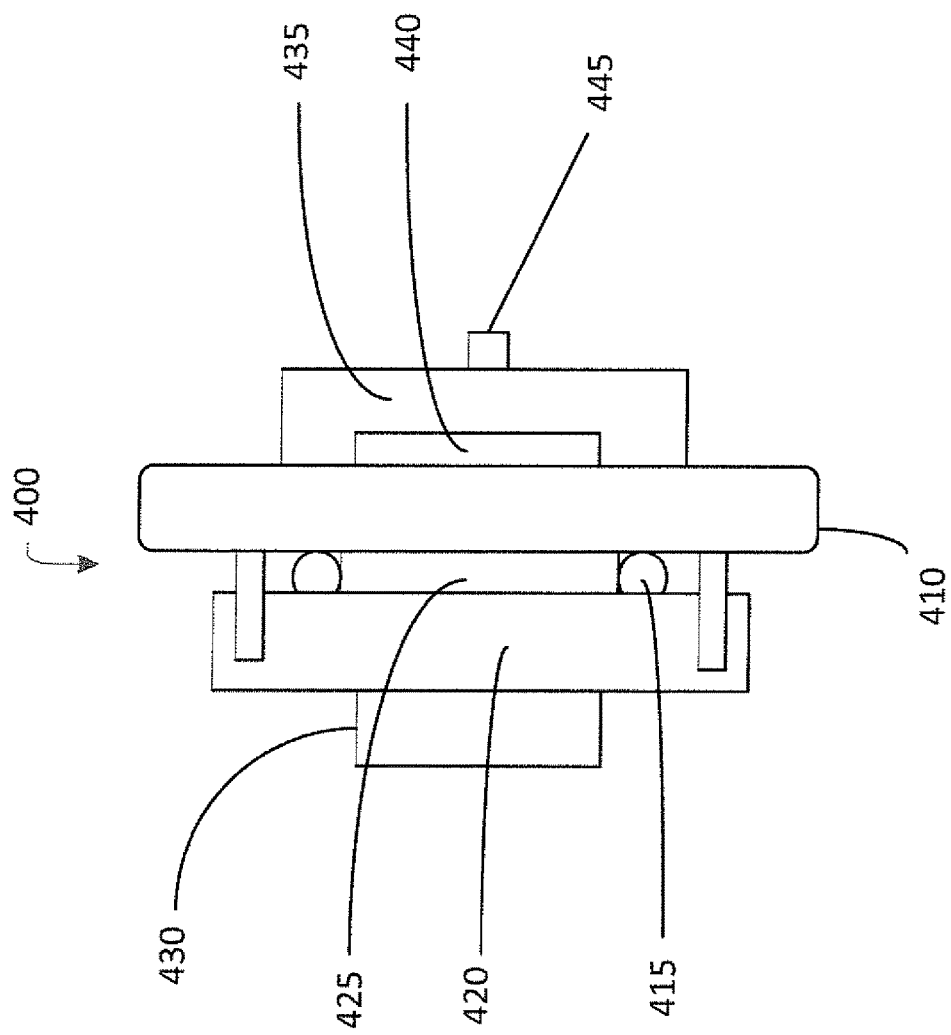
FIG. 4 illustrates an exemplary electroacoustic transducer mechanical alignment stage.

FIG. 4 illustrates an exemplary electroacoustic transducer mechanical alignment stage 420 disposed between electroacoustic transmitter and receiver units 430, 435. Piezoelectric element 440 is placed on the front face of electroacoustic receiver unit 435 which converts the acoustic energy to electrical and transferred to receiver output 445. Alignment is achieved by inserting acoustic coupling medium 425 into mechanical alignment flanges 415. The transmitter transducer 420 transmits acoustic energy of waveforms comprising continuous or pulsed width with variable duty cycle, pure sine waves, square waves, triangular waves or an arbitrary repetitive shape.

Acoustic coupling medium 425 can be a gel pad, ultrasound coupling pad, liquid, or a gas. The primary criterion in choosing an acoustic coupling medium is matching acoustic impedance(s) so that power transmission is maximized with a low loss material. Exclusion of air is also desired because air attenuates (lossy) ultrasound over frequencies of 100 kHz. Charging pad surface 410 maintains relatively parallel geometries for alignment.

Figure 5:
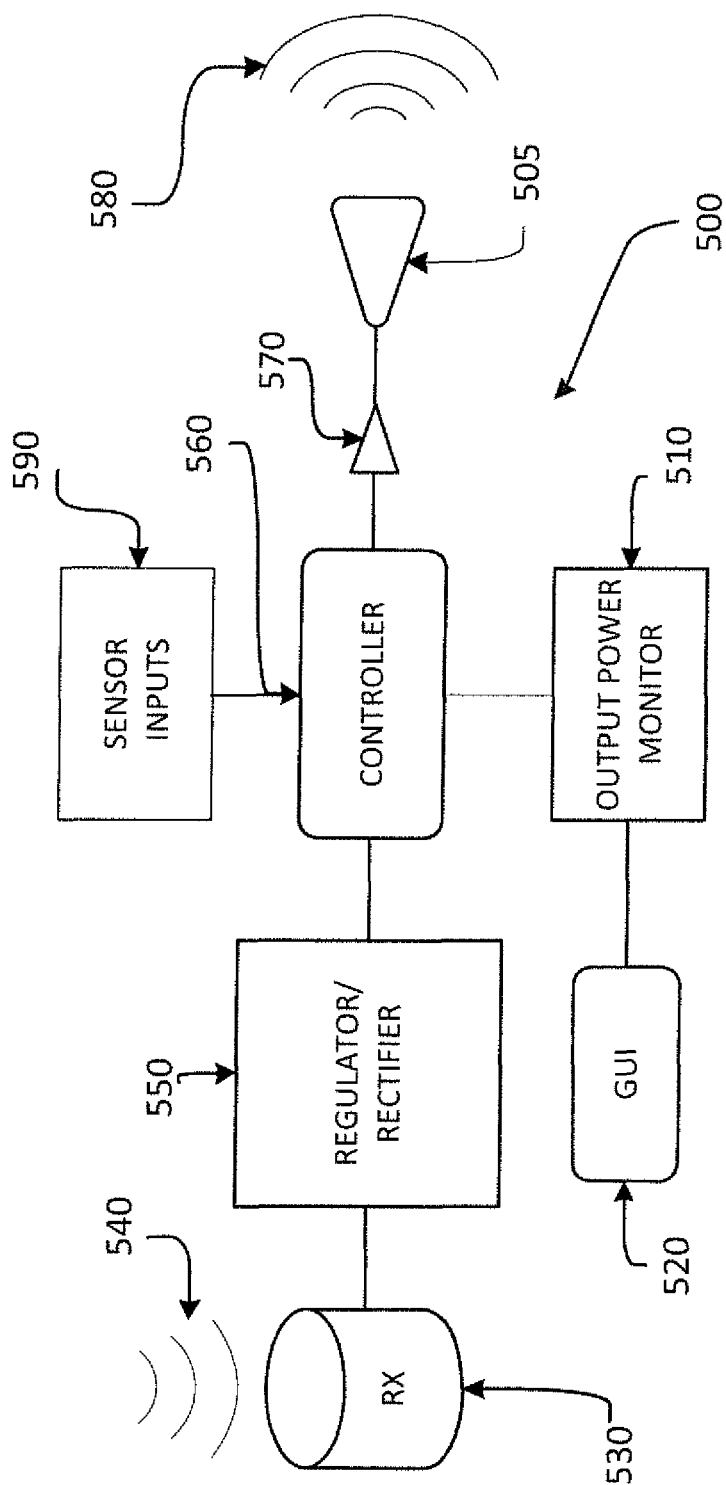
FIG. 5 illustrates an exemplary receiver module an electroacoustic charging system.

FIG. 5 illustrates the feedback loop of an exemplary receiver module 500 an electroacoustic charging system. Receiver module 500 comprises electroacoustic receiver controller 560, graphic user interface 520, regulator/rectifier 550, output power monitor 510, sensor inputs 590, receiver transducer 530 and electromagnetic antenna 505. Data is collected and stored as parameters which is then transmitted over electromagnetic antenna 505 as an electromagnetic signal 580. The feedback loop is used to maximize acoustic power transmission 540 and monitor the health of the circuit. Power is monitored 510 and displayed at the GUI 520.

FIG. 6 demonstrates the selective activation of an exemplary transducer array of an electroacoustic charging system 600. In the present embodiment, feedback looping is used to activate transducers which are proximal to portable devices for charging. As can be seen, portable device 610 is being charged through receiver transducer 640 from transmission transducers 650-651. Portable device 620 is receives acoustic power through receiver transducers 641, 642 via transmission transducers 653-654. Portable device 630 is receives acoustic power through receiver transducers 643, 644 via transmission transducers 657-659. To conserve power, transducers 652, 655 and 656 are not activated.

FIG. 7 is the top down view of an exemplary transducer array 700 of an electroacoustic charging system with an exaggerated receiver transducer 710 in accordance with the present embodiment. There are two geometrical issues affecting alignment of a transmitter to the receiver in both the electromagnetic and ultrasound methods. The first is lateral translation over the receiver. The second is angular misalignment between the transmitter and receiver. The use of an array transmitter enables compensation for both of these misalignments. The voltage, current and/or power out of the receiver is a signal fed back to the external controller which commands the array transmitter to search for the optimum alignment. In another embodiment, an imaging ultrasound system is added to the transmitter unit to provide the feedback on the depth and orientation of the receiver, thereby assisting alignment. This may compensate for misalignment but may not search for a receiver in some designs.

FIG. 8 projects an isometric view of an exemplary two-dimensional ultrasonic transducer array 820 of an electroacoustic power pad 800 for the purposes of charging in a non-mechanical alignment environment. In one or more embodiments two dimensional arrays are used for the purposes of non-mechanical alignment. A phased array is an array of transducers in which the relative phases of the respective signals feeding the transducers are varied in such a way that the effective radiation pattern of the array is reinforced in a desired direction and suppressed in undesired directions.

To keep the temperature of a device within tolerances, a cooling device such as a circulating-liquid heat exchanger may be provided. One or more Peltier coolers, miniature high-capacity fans, or other methods can be attached to or nearby the transmitter/receiver assembly. Temperature sensing devices within the transmitter and receiver may relay temperatures to the external controller, which will then apply the correct power to the cooling device in order to keep the temperature of the transmitter and receiver unit, and application under charge at safe values.

Piezoelectric elements of the transmitter and receiver may be monolithic elements of piezo ceramics, composite materials, polymers or other emerging materials. They may be one- or two-dimensional arrays of small piezoelectric elements of the same variety of materials. Capacitively Machined Ultrasound Transducers (CMUTs) or other mechanisms for inducing ultrasound vibrations are an alternative to conventional piezoelectric elements. In one embodiment, a 2-dimensional array can be used to provide non-mechanical alignment of transmitter and receiver in response to optimization signals generated within the receiver unit and relayed back to the transmitter.

In one environment, high temperatures, CMUTS are especially attractive, because temperatures of over 150 C can cause piezoelectric elements to fail. CMUTS can withstand temperatures up to 800 C and several atmospheres of pressure. So they are attractive options for engine compartment environments. They can also be easily made into arrays that can be used for wavefront steering.

FIG. 9 depicts an exemplary temporal abstraction of the side view of 2-dimensional electroacoustic phased array 920 and corresponding wavefront steering for non-mechanical alignment. In the present embodiment, signals 930 propagating from phased array 920 are differentiated by a constant phase 910. The result is a beam steered acoustic wavefront 940, which can be directed towards a portable device for the purposes of charging.

For angular alignment two effects are considered. The first of these is the turning of the beam's wave front from parallel to the face of the transmitter array, through an angle that makes the wave front parallel to the face of the receiver. This compensates for angular misalignment of the faces of the two transducers. For two dimensional surfaces this needs to be done along two axes. It is well known to those skilled in the art that this is accomplished by embedding a constant time differential, which results in a phase difference, between each element of the array.

FIG. 10 illustrates an abstraction circuit used to produce electrical signals delivered to 2-dimensional electroacoustic phased arrays. Clock 1010 supplies a timing standard to phase shifters 1025-1035. Relative phase is received from beam position and feedback controller 1080 and sent to amplifiers 1060 which are tied to power supply 1020. The amplified signals drive acoustic transducers 1050 in accordance with the latest embodiment. Transmitted power information 1040 is scanned and communicated back to beam position and feedback controller 1080 through electromagnetic antenna 1070. Phase can then be adjusted to maximize transmitted power to portable device.

FIG. 11 illustrates the side view of an exemplary electroacoustic charging cover 1100 to be used with any generic portable device 1110. Electroacoustic charging cover adapts to any generic portable device 1110 using its charging port (e.g., USB) 1140 through the electroacoustic charging cover 1100 interface 1130. Charging or direct power is accomplished through piezo element and conversion circuitry 1120.

In an aspect, the present concepts may be applied to an existing market which needs retrofit batteries; in another aspect, the present concepts may be applied to a market where ultrasonic rechargeable batteries are integrated into the fabrication process of phones. The ability to add a retrofit battery pack to any cell phone can be useful. The battery pack contains piezoelectric elements that convert mechanical stress to electrical energy. The small pack sends the electrical energy to the battery inside the cell phone. This can eliminate the need to replace existing cell phone batteries with piezo batteries. Again, those skilled in the art will appreciate that the present exemplary device of a cellular phone can equally be generalized to cover other personal data devices such as personal digital assistants, gaming devices, communication platforms and mobile computers and tablets. In other words, electroacoustic elements that convert mechanical energy to electrical energy are designed within the battery packs, to which existing personal devices can be connected. Other personal data devices may have incorporated within them, the electromechanical receiver element or elements as well as the associated circuitry, which is activated by an external matched transmitter source.

FIG. 12 depicts top and side views of an exemplary electroacoustic charging system comprising electroacoustic power pad 1210 and cell phones 1230, 1220. Cell phones 1220, 1230 have piezo receiver elements 1240, 1250 integrated therein. Charging pads can be of sizes to accommodate one, two, or several devices at a time. The upper side view shows the latter case which the transmitter pad is made up of many independent piezo elements. These sense when a receiver is over them. Only those elements are then active. This keeps power requirements low and reduces heating of the pad and device. A soft cover can be used to avoid air in the interface with receiver. The charging pad houses transmitter elements, electronics and connection to a wall plug for input power. A pad that could accommodate several small appliances would be from 4 to 6 inches wide and from 6 to 8 inches long. and ½ to 1 inch thick. One inch square comprises approximately 20 to 45 such piezos. In another embodiment the entire pad comprises a single ultrasound producing element. This can be a piezoelectric material, CMUTS or flexible polymer PVDF.

FIG. 13 depicts top and side views of an exemplary electroacoustic charging system comprising electroacoustic power pad 1300 and portable devices 1310 according to an alternate embodiment. Portable devices 1310 are inserted into charging ports 1340 and held in place with soft springs whereby they are acoustically coupled to ultrasonic transducers 1420 through coupling media 1330. The present configuration is desirable due to the exclusion of air at the boundary layer.

When a device is placed on the pad, the transmitter elements send out ultrasound signals, and powers up the receiver, which returns a signal to the pad indicating it is there. The proper transmitter elements are then activated to perform charging. Alternately a proximity switch senses where the phone or battery is on the pad and piezos are activated only around the device. This way power is not lost when all piezos are activated. Only the ones around the device are activated. Then a signal goes from receiver to transmitter when the battery is fully charged.

FIG. 14 illustrates in-situ autonomous sensor charging of an electroacoustic system 1400 in a modern automobile according to an additional embodiment of the present invention. In the automobile industry, ultrasound power delivery will decrease costs and increase safety. Ultrasound recharging may be a power saving method in cases where sensors 1410, 1420, 1430 and transmitters are close to one another. However, the ability of recharging without running wires, like in car or truck doors, will save manufacturers money and reduce maintenance issues. Another embodiment attaches a stage via a slight suction generated by a boot and clamp method, as used for affixing items to the inside of an automobile windshield. A manual adjustment method, in one embodiment, uses three screws of fine pitch set in a triangle, which aligns the platform transmitter angularly over the receiver.

According to one embodiment, low-frequency ultrasound is used to illuminate one or more receivers in vibrational energy. The only limitation on the ultrasound frequency is its ability to penetrate a few feet of air without significant absorption. The receivers would convert vibrational energy into electrical energy. This is stored near the sensors or used in real time and functions like an RF-ID system. A few acoustic transmitters strategically positioned in places in the engine compartment, trunk and body can deliver power to a majority of the sensors of interest. The acoustic transmitters are powered from the main automotive battery or the power train itself. The availability of significant amount of power for transmitters will compensate for receiver inefficiencies. Issues of personnel safety can be avoided by appropriate placement of the transmitters, avoiding for example propagating through the auto's passenger compartment.

FIG. 14 illustrates a cutaway of an auto 1400 with a variety of sensors 1410-1440 and receivers/transceivers (triangles) that pertain to the suspension and steering. The sensors and receivers may be in close proximity to one another. Or, the receivers may be tethered to the sensors and in a location more favorable to reception of the incoming ultrasound. Illustrated are the possible placements of a few ultrasound transmitters (diamonds) that may provide power to several sensors simultaneously. In one embodiment, the ratio of the frequency and size of the transmitters will be chosen so that the ultrasound is emitted over a large cone angle that contains the receivers of several sensors. Because ultrasound transducers can be made thin, less than 5 mm in thickness, they can fit up against flat panels in the compartments where they are mounted.

In the oil and gas industry, recharging batteries for undersea sensors or other applications is expensive requiring waterproof connections for the recharging lines, and dangerous because electrical recharging equipment can cause sparks which could lead to fires or explosions. Underwater compliant contact connections can be used with ultrasound to transmit to a receiver without an electrical connection and wirelessly, increasing safety and reducing cost.

FIG. 15 illustrates a cutaway and diagrammatic view of a rim and axle that includes a direct tire pressure monitoring system (DTPMS) 1500 that includes one or more ultrasonic transducer components, as described herein. The DTPMS 1500 includes a stationary transceiver 1510 that includes at least one transmitter acoustical element 1511 and a movable transponder 1520 that includes at least one receiver acoustical element 1521. The transmitter and receiver acoustical elements 1511, 1521 can be or can include a piezoelectric material or element.

The stationary transceiver 1510 is mounted on or attached to a non-rotating member 1530 of the wheel suspension system, such as an axle. The stationary transceiver 1510 is disposed at a location close or proximal to wheel hub 1540. In one example, the stationary transceiver 1510 is disposed about 5 cm to about 30 cm from wheel hub 1540. In another example the stationary transceiver 1510 is disposed about 10 cm to about 25 cm from wheel hub 1540, about 15 cm to about 20 cm from wheel hub 1540, or any value or range between any two of the foregoing values. As used herein, "about" means plus or minus 10% of the relevant value or number. The stationary transceiver 1510 can be powered by a local battery unit or by the vehicle's main battery. The movable transponder 1520 is mounted on or attached to the wheel rim 1550 by a strap 1525 where it is exposed to the internal tire pressure of a tubed or a tubeless tire (not illustrated) mounted on the rim 1550. The strap 1825, which can securely pull a first side (e.g., an unexposed side) of movable transponder 1520, such as a first side of a movable transponder housing, against the wheel rim 1550 so that the first side of movable transponder 1520 is in direct physical contact with the wheel rim 1550 to receive ultrasonic energy transmitted by stationary transceiver 1510. The wheel rim 1550 is mounted on break rotor 1560, which is as a rotating part of the wheel hub 1540.

In operation, stationary transceiver 1510 generates ultrasound energy though transmitter acoustical element 1511, which travels through the non-movable member(s) 1530 of the wheel suspension system, break rotor 1560, and wheel rim 1550 to receiver acoustical element 1521 where it is converted into electrical energy, which is used to power one or more sensor(s) 1522 on the movable transponder 1520. Thus, the movable transponder 1520 operates as a power adaptor to transform acoustical energy into electrical energy for the sensors 1522. In some embodiments, the ultrasound energy generated by stationary transceiver 1510 forms a standing wave pattern as a function of the ultrasound energy frequency. In some embodiments, the stationary transceiver 1510 is configured to generate a standing wave pattern of ultrasonic energy such that the movable transponder 1520 is located at a high-energy node of standing wave to enhance or maximize energy transfer to the movable transponder 1520. One skilled in the art will understand that standing waves can be formed on two-dimensional surfaces (e.g., on a Chiandi plate) as well as on or in three-dimensional surfaces, such within a structure of a vehicle as described herein. In general, a standing wave pattern provides regions of high and low amplitude energy (e.g., nodes and antinodes, respectively).

In some embodiments, the stationary transceiver 1510 is configured to generate progressive longitudinal waves and/or shear waves of ultrasonic energy. The standing wave, progressive longitudinal waves, and/or shear waves of ultrasonic energy are transmitted through the solids (metal and/or non-metal solids) and liquids/gel-like media (e.g., lubricants, coupling media, etc.) in the vehicle between stationary transceiver 1510 and movable transponder 1520. In general, the ultrasonic energy does not pass through the surrounding air due to the impedance mismatch at the solid-air (or liquid/gel-like media-air) boundary.

The sensors 1522 can measure the tire pressure, temperature, wheel imbalance, gas composition, or other property of the tire or wheel. In some embodiments, the sensor(s) 1522 include a pressure sensor diaphragm disposed on an exposed face 1523 of stationary transceiver 1510. The movable transponder 1520 transmits the data sensed by the sensor(s) 1522 to stationary transceiver 1510, which is in electrical communication, directly or indirectly, with the vehicle's control system 1575. The data can be transmitted (e.g., digitally) through a variety of means, for example RF transmission or keyed acoustical impedance changes of the ultrasound energy harvesting by movable transponder 1520. The sensor(s) 1522 can operate continuously (e.g., in real-time) or in an intermittent mode. Likewise, the movable transponder 1520 can transmit the data obtained from sensor(s) 1522 continuously (e.g., in real-time) or in an intermittent mode. Alternatively, the movable transponder 1520 can acquire and/or transmit data from a first sensor continuously but acquire and/or transmit data from a second sensor in an intermittent mode. In addition or in the alternative, the movable transponder 1520 can push data to stationary transceiver 1510 on a continuous or on an intermittent basis, or the stationary transceiver 1510 can poll/pull data from the movable transponder 1520 on a continuous or intermittent basis.

The vehicle's control system 1575 includes a central processing unit that can analyze the received data, display some or all of it to the motorist, and generate an alarm if the received data is out of an operating tolerance window, or greater or lower than a predetermined threshold value. For example, if the received data indicates that the tire pressure is lower than a predetermined value (e.g., less than 25 psi), the vehicle's control system 1575 can generate an alarm. In some embodiments, the predetermined value is variable based on the internal temperature of the tire, which can be monitored by one of sensors 1522 or another sensor. For example, the predetermined threshold value for tire pressure can be about 25 psi to about 35 psi (or any value or range therebetween) when the tire is cold (e.g., less than about 75 deg. F.) but it can be higher (e.g., about 30 psi to about 40 psi, or any value or range therebetween) when the tire is hot (e.g., greater than about 120 deg. F.). The predetermined threshold value for tire pressure can be higher or lower depending on the vehicle. For example, larger passenger vehicles, such as full-size pickups and sport utility vehicles, can have a higher predetermined threshold value for tire pressure, such as about 30 psi to about 45 psi (or any value or range therebetween), when the tire is cold, and about 35 to about 55 psi (or any value or range therebetween) when the tire is hot. In another example, the predetermined threshold value for tire pressure can be up to about 115 psi when the tire is cold for large trucks, such as tractor trailers, semi-trailers, construction vehicles, etc.

Each wheel/tire of the vehicle can be equipped with its own DTPMS 1500 so each tire can be monitored individually in the manner described above. Using ultrasound transmitted through the solid metal members 1530 of the suspension and wheel system addresses some or all of the problems of conventional direct TPMSs, as discussed above, and can add the potential for more comprehensive sensing and monitoring in real-time. In addition, the moveable transponder 1520 described herein does not require a battery, which may be subject to drain or failure, thus enhancing the reliability of the system. For example, moveable transponder 1520 can receive energy from stationary transceiver 1510 continuously, thus obviating the need for a battery. In some embodiments, moveable transponder 1520 includes a capacitor or other temporary energy-storage device that can temporarily store energy, which may be needed in case of a short or momentary lapse in energy transfer from stationary transceiver 1510. The stationary transceiver 1510 can be powered by the vehicle's main battery, by a separate battery unit, or continuously from electrical power generated by the vehicle's alternator.

The stationary transceiver 1510 and movable transponder 1520 can include some or all of the components and function(s) of electroacoustic transmitter 210 and electroacoustic receiver 225, respectively, as discussed above, with the exception that moveable transponder 1520 includes a capacitor (or other temporary energy-storage device) in place of battery 220, for example as described below with reference to FIG. 16.

FIG. 16 illustrates a block abstraction of an electroacoustic direct tire pressure monitoring system (DTPMS) 1600 comprising a stationary transceiver 1610 and a movable transponder 1620. The stationary transceiver 1610 and movable transponder 1620 include the same or similar components as electroacoustic transmitter 210 and electroacoustic receiver 225, respectively, as discussed above, with the exception that moveable transponder 1620 includes a capacitor 1602 in place of battery 220. The capacitor 1602 can store a quantity of energy to power the moveable transponder 1620 for a brief period, such during a momentary blackout or brownout. In some embodiments, capacitor 1602 is a filter capacitor that forms a portion of rectifier 215. In other embodiments, capacitor 1602 is a separate and distinct component from rectifier 215. In some embodiments, power source 1680 is the vehicle's battery, a separate battery unit, or the vehicle's alternator.

In addition, stationary transceiver 1610 and movable transponder 1620 can be the same as or similar to stationary transceiver 1510 and movable transponder 1520, respectively.

FIG. 17 illustrates a detailed cutaway of the non-rotating member 1530 of the suspension system and break rotor 1560 to illustrate the path of ultrasound energy between the stationary transceiver 1510 and the movable transponder 1520. As illustrated, a plurality of bearings 1700 are disposed between the non-rotating member 1530 and break rotor 1560. Each bearing 1700 includes a rolling bearing element 1710 disposed between an inner race 1720 and an outer race 1730. The inner race 1720 is attached to non-rotating member 1530 and the outer race 1730 is attached to break rotor 1560. A thin film of lubricant 1740 is disposed around the rolling bearing element 1710 to provide lubrication thereto. The thin film of lubricant 1740 can have a cross-sectional thickness of about 1 micron or less. In other words, there can be about 1 micron or less of lubricant 1740 between rolling bearing element 1710 and inner race 1720 and about 1 micron or less of lubricant 1740 between rolling bearing element 1710 and outer race 1730.

As can be seen, ultrasonic energy can be transmitted between each component of the foregoing, which provides a continuous physical medium for ultrasonic energy to pass between (e.g., to/from) stationary transceiver 1530 and movable transponder 1520 (not illustrated). For example, ultrasonic energy generated by stationary transceiver 1530 can be transmitted to movable transponder 1520 along a path 1750. The path 1750 extends from stationary transceiver 1510 through non-rotating member 1530, inner race 1720, lubricant 1740, rolling bearing element 1710, lubricant 1740, outer race 1730, and break rotor 1560 to movable transponder 1520. As discussed above with respect to FIG. 15, movable transponder 1520 is mounted on wheel rim 1550, which is mounted on break rotor 1560.

FIG. 18 illustrates a movable transponder 1820 that includes a pressure sensor 1822 for measuring the air pressure of a tubeless tire 1800. The movable transponder 1820 is attached to or mounted on wheel rim 1850 by a strap 1825, which can securely pull a first side (e.g., an unexposed side) of movable transponder 1820, such as a first side of a movable transponder housing, against the wheel rim 1850 so that the first side of movable transponder 1820 is in direct physical contact with the wheel rim 1850 to receive ultrasonic energy generated by a stationary transceiver.

The pressure sensor 1822 is disposed on a second side (e.g., an exposed side) of movable transponder 1820, such as a second side of a movable transponder housing. The pressure sensor 1822 can include a pressure sensor diaphragm in some embodiments. As illustrated, the pressure sensor 1822 is exposed to the internal pressurized cavity 1805 defined by tubeless tire 1800 and thus can directly measure the air pressure of tubeless tire 1800. Movable transponder 1820 and pressure sensor 1822 can be the same as, similar to, or different than movable transponders 1520, 1620 and pressure sensor 1522, described above.

FIG. 19 illustrates a movable transponder 1920 that includes a pressure sensor 1922 for measuring the air pressure of a tubed tire 1900. The movable transponder 1920 is attached to or mounted on wheel rim 1950 by a strap 1925, which can securely pull a first side (e.g., an unexposed side) of movable transponder 1920, such as a first side of a movable transponder housing, against the wheel rim 1950 so that the first side of movable transponder 1920 is in direct physical contact with the wheel rim 1950 to receive ultrasonic energy generated by a stationary transceiver.

The pressure sensor 1922 is disposed on a second side (e.g., an exposed side) of movable transponder 1920, such as a second side of a movable transponder housing. The pressure sensor 1922 can include a pressure sensor diaphragm in some embodiments. As illustrated, the pressure sensor 1922 senses pressure exerted by tube 1910 of tubed tire 1900. For example, tube 1910 can press against pressure sensor 1922 (e.g., a pressure sensor diaphragm), which allows pressure sensor 1922 to measure the internal air pressure of tube 1910. Movable transponder 1920 and pressure sensor 1922 can be the same as, similar to, or different than movable transponders 1520, 1620, 1820 and pressure sensors 1522, 1822 described above.

FIGS. 20-23 are flow charts that illustrate different aspects of configuring a DTPMS to generate ultrasound energy that provides a desired standing wave, progressive longitudinal waves, and/or shear waves of ultrasonic energy. FIG. 20 is a flow chart 2000 for designing a testing apparatus and transmitter driver and mapping the parameter field of a DTPMS. The physical construct of a piezo-electric transmitter-receiver for energy transfer as well as detailed modal analysis can be numerically simulated using one of several commercial modeling tools, such as those available from The MathWorks, Inc. (e.g., MATLAB®), COMSOL Inc. (e.g., COMSOL Multiphysics®), ANSYS, Inc., and others. In addition, the physical can be modeled numerically to generate the optimal energy transfer, based on a series of source-receiver conditions, while including different intervening layers of media.

In step 2010, an ultrasonic energy driver for the stationary transceiver is designed according to one or more inputs, such as the range of optimal node spacing of the desired standing wave of ultrasonic energy (and/or other desired properties of progressive longitudinal waves and/or shear waves of ultrasonic energy). The design determined in step 2010 includes a desired frequency range for the ultrasonic energy, the operating power levels of the ultrasonic energy, the type or form of the ultrasonic transducers. The design determined in step 2010 can also include the form of ultrasound energy transmission (e.g., standing wave, progressive longitudinal waves, shear waves, or a combination of any of the foregoing). After the ultrasonic energy driver is designed or provided, the operating parameters are characterized in step 2020. For example, in step 2020, the operating frequency range and power levels of the ultrasonic energy are systematically scanned.

In one example, the characterizations in step 2020 can occur when the stationary transceiver and the movable transponder of the DTPMS are mounted on the appropriate locations on the vehicle, as described above. In another example, the characterizations in step 2020 can occur when the stationary transceiver and the movable transponder of the DTPMS are mounted on a bench apparatus, for example on a steel plate, to model the expected behavior of the system. The stationary transceiver can then scan through its potential range of operating ultrasound frequencies at each of its operating power levels. The parameters of the DTPMS can then be measured and logged, such as the resonance frequencies of the vehicle, the node distribution of the standing wave produced at each frequency and power level, and the amount of ultrasound energy that the movable transponder can harvest. Other parameters can include the properties of the progressive longitudinal waves and/or shear waves of ultrasonic energy, the resultant energy transfer, and other parameters, if progressive longitudinal waves and/or shear waves of ultrasonic energy transfer are used instead of or in addition to standing waves. The result of step 2020 is a data table that includes the foregoing parameters. A data acquisition system can be connected to or in electrical communication with the movable transponder to collect the foregoing data.

In the example of a standing wave pattern of ultrasound energy transfer, this parameter data provides a general map of the standing wave pattern in the vehicle in the vicinity of the DTPMS (e.g., along path 1750) or in the bench test sheet. The standing waver pattern is a function of the ultrasound frequency and resonance frequency of the materials through which the ultrasound energy passes (e.g., bench apparatus or components of the vehicle in the vicinity of the DTPMS, such as along path 1750). Specifically, there will be resonance frequencies where the wave pattern "stands" and does not change over time. At frequencies different from resonance frequencies the modes will be "stirred" meaning they will rapidly change over time with the result that no clear patterns emerge and the sheet vibrations appear chaotic. This is an undesirable condition as the amplitude at "nodes" will be comparatively small, rendering the energy transfer process less efficient. In contrast, at resonance frequencies, there will form well-defined nodes and troughs of vibrational modes. The spacing of these nodes will shrink as the frequency is increased. Evaluating the pattern change with frequency and transmitting transducer shape and size will be part of mapping out the parameter field. Scanning through the amplitude of the energizing ultrasound energy into the transmitting transducer will initially be substantially linear but may become non-linear at a higher power.

In addition or in the alternative, the parameter data provides a general map of the progressive longitudinal wave and/or shear wave pattern(s) in the vehicle in the vicinity of the DTPMS (e.g., along path 1750) or in the bench test sheet, which can be used to optimize energy transfer.

FIG. 21 is a flow chart 2100 for designing a testing station and transmitter driver and mapping the parameter field of the stationary transceiver. In step 2110, a suitable transmitter driver is designed. The transmitter driver can be based on one or more inputs, such as the range of optimal node spacing and the ultrasound energy power requirement. These inputs can be provided based on the parameters collected and analyzed in step 2020.

In step 2120, the stationary transceiver is mounted in a vehicle or mounted on a bench apparatus, such as a steel plate, to simulate a vehicle. The movable transponder is not mounted in step 2120. The stationary transducer is then scanned through its operating frequency range and power levels to characterize the system. Examples of data/parameters collected are resonance frequencies and node distributions, as measured with a testing apparatus. In some embodiments, the testing apparatus can also measure the ultrasonic energy that can be harvested at each frequency and power level at the location of the testing apparatus (e.g., on the wheel rim or on the bench apparatus).

The output of step 2120 is a parameter data table of the system's impedance in an unloaded state (i.e., without the movable transponder in place). This can serve as a reference to compare the unloaded system to a loaded system where the movable transponder is in place.

FIG. 22 is a flow chart 2200 for optimizing the ultrasound energy transfer from the stationary transceiver to the movable transponder. In step 2210, the DTPMS system is set up, preferably mounted on a vehicle, as described above. In step 2220, the stationary transceiver cycles through a plurality of ultrasound energy frequencies at a minimum operating power level to measure the system impedance and to determine an impedance minimum while the movable transponder is in a stationary position. With the movable transponder in place, the system impedance can change from the impedance measured in 2120. In general, a lower impedance represents a stronger energetic coupling while a higher impedance represents a weaker coupling.

If an impedance minimum is not found in step 2220, the power of the stationary transceiver is incrementally increased at step 2230 and the stationary transceiver again cycles through a plurality of ultrasound energy frequencies at the increased power level. This process continues until an impedance minimum is found. When an impedance minimum is found, the flow chart 2200 proceeds to step 2240 to establish two-way communication between the stationary transceiver and the movable transponder. The stationary transceiver can form an ultrasound signal modulated with an echo-request packet. The modulation may be one of the common analog modulation schemes such as amplitude modulation (AM), frequency modulation (FM), phase modulation (PM), quadrature amplitude modulation (QM), space modulation (SM), single sideband modulation (SSB) or one of the common digital modulation schemes, such as amplitude shift keying (ASK), asymmetric phase-shift keying (APSK), continuous phase modulation (CPM), frequency-shift keying (FSK), multiple frequency-shift keying (MFSK), minimum-shift keying (MSK), on-off keying (OOK), pulse-position modulation (PPM), phase-shift keying (PSK), quadrature amplitude modulation (QAM), single-carrier frequency-division multiple access (SC-FDMA) or trellis coded modulation (TCM). Some of these modulation schemes require more than one transmitting source and would therefore only be applicable when the stationary transceiver and/or the movable transponder includes a plurality of transducers. The effectiveness of the modulation schemes can vary as understood by those skilled in the art. Alternatively, the stationary transceiver can communicate using electromagnetic signals. When the movable transponder, which is programmed to listen and respond to specific commands or requests, responds then communication is established. If not, an error flag should be raised.

As discussed above, communication from the stationary transceiver to the movable transponder can be facilitated through a modulation scheme of the ultrasound energy. The movable transponder demodulates (e.g., through hardware and/or software) the transmitted ultrasound energy to determine the signal(s) or command(s) communicated thereby. Communication from the stationary transceiver to the movable transponder occurs through impedance changes "seen" by the movable transponder. To facilitate this direction of the communication, the movable transponder can be enabled, through hardware and software engineering, to modulate the load that the movable transponder presents to the stationary transceiver. The impedance may then be varied according to any of the above-mentioned modulation schemes, if deemed suitable. As discussed, the stationary transceiver is enabled, through hardware and software engineering, to demodulate the seen impedance changes. In some embodiments, the foregoing can be achieved or supplemented by theoretical and/or numerical analyses.

FIG. 23 is a flow chart 2300 for dynamically optimizing the ultrasound energy transfer from the stationary transceiver to the movable transponder while the movable transponder is in motion. After bi-directional communication with the movable transponder has been established and power transfer has been optimized while remaining stationary in flow chart 2200, a loop process may be implemented to maintain optimal power transmission during varying operating conditions. For example, a first operating condition can be when the vehicle is in idle (e.g., about 500 to about 1,000 RPMs). A second operating condition can be when the vehicle is accelerating (e.g., about 2,000 to about 3,000 RPMs). In another example, a first operating condition can be when the vehicle is in idle and other operating conditions can be when the vehicle is travelling at different speeds (e.g., at 15 mph, at 30 mph, at 45 mph, at 60 mph, etc.) and/or on different road conditions (e.g., smooth pavement, dirt road, etc.). The vibrations in the vehicle caused by the engine, the rotational speed of the wheels, the suspension, and/or the road conditions may affect the power transmission. Thus, the initial "stationary" operating parameters (frequency, power level) from the first operating condition may be adjusted as illustrated in flow chart 2300 in a "dynamic tracking" process to maintain optimal power transmission conditions even as the operating conditions change.

In step 2310, the system is tested for an impedance minimum, for example at an initial ultrasound frequency, which may be the same as the initial "stationary" ultrasound frequency that had an impedance minimum found in step 2220. The flow chart 2300 is a continuous loop where the ultrasound frequency is repeatedly or constantly being changed (i.e., decreased in step 2320 or increased in step 2330) around the optimum impedance value. If there is a change in the system that changes the optimal operating parameters, this loop will track these changes, provided the time constant of the system changes are small compared to the time constant of the loop. However, since the loop may process at speeds of a substantial percentage of the ultrasound carrier wave frequency, any practical change in the operating conditions of the DTPMS (e.g., stationary transceiver and/or movable transponder) may be slow compared to the process loop speed and thus may not even be perceptible by the user.

FIG. 24 is a cutaway and diagrammatic view of a shock absorber 2400 of a vehicle suspension system that includes that includes one or more sensors coupled to ultrasonic transducer components, as described herein. A first sensor system 2405 includes an ultrasound transceiver 2410 and an ultrasound transponder 2420. The transponder 2420 includes one or more sensors 2422 electrically coupled thereto. The sensors 2422 can measure various properties of high-pressure gas chamber 2425 of shock absorber 2400, such as its pressure and/or temperature. The ultrasound transceiver 2410 and ultrasound transponder 2420 are disposed on opposing sides of tubular housing 2450 of shock absorber 2400. Tubular housing 2450 can be formed of or can include steel or other material as known in the art. Tubular housing 2450 provides a physical medium through which ultrasonic energy can pass between the ultrasound transceiver 2410 and ultrasound transponder 2420, similar to the embodiments described above. In some examples, ultrasound transceiver 2410 and/or ultrasound transponder 2420 generate a standing wave (and/or progressive longitudinal waves and/or shear waves) of ultrasound energy that optimizes power transfer and that provides a carrier wave that can be modulated to transmit information or commands. For example, ultrasound transponder 2420 can convert ultrasound energy received from ultrasound transceiver 2410 to provide electrical energy for the sensors 2422 coupled to ultrasound transponder 2420. The data from sensors 2422 can then be transmitted from ultrasound transponder 2420 to ultrasound transceiver 2410 generate ultrasound energy by modulating ultrasound energy waves generated by ultrasound transponder 2420.

A second sensor system 2460 is also illustrated in FIG. 24. The second sensor system 2460 includes an ultrasound transceiver 2470 and an ultrasound transponder 2480. The transponder 2480 includes one or more sensors 2482 electrically coupled thereto. The sensors 2482 are configured to measure one or more properties of oil reservoir 2475, such as its temperature and/or the volume of oil in the oil reservoir 2475. Energy transfer and communication between ultrasound transceiver 2470 and ultrasound transponder 2480 is the same as or similar to the energy transfer and communication between ultrasound transceiver 2410 and ultrasound transponder 2420, described above.

As can be seen, the foregoing first and second sensor systems 2405, 2460 allow the vehicle to monitor certain locations and properties of the shock absorber 2400 that could not be monitored using conventional systems. For example, conventional systems that communicate using electromagnetic wireless signals could not pass such signals through tubular housing 2450 which is generally formed of steel. In addition, conventional systems require a battery to power the transponders and sensors, but the remote location of transponders 2420, 2480 would make battery replacement impractical.

Another aspect of the invention is directed to providing ultrasound energy and converted electrical power to remote sensors in various industries. Examples of such industries include oil and gas, such as offshore oil and gas, chemical, dairy, food, and nuclear industries.

FIG. 25 is a cross section of a system 2500 for providing ultrasonic energy and converted electrical power to a sensor in an electrically-conductive metallic pipe 2510. The system 2500 includes an ultrasound transceiver 2520 and an ultrasound receiver transponder 2530. The ultrasound transceiver 2520 is mounted on an external surface 2514 of a wall 2512 of metallic pipe 2510. The ultrasound receiver transponder 2530 is mounted on an internal surface 2516 of the wall 2512 of metallic pipe 2510. The metallic pipe 2510 can comprise various steels, Fe-alloys, Al, Ti, Cu, and/or Cu—Zn—Sn alloys. The transceiver 2520 and the receiver transponder 2530 are aligned on the wall 2512 of the pipe 2510. For example, the transceiver 2520 can be disposed at a transceiver location on the external surface 2514 of the wall 2512 and the receiver transponder 2530 can be disposed at a transponder location on the internal surface 2516 of the wall 2512, where the transceiver location corresponds to the transponder location. In some embodiments, the transceiver location and the transponder location are on opposing sides of the wall 2512, for example as illustrated in FIG. 25. The wall 2512 can be thick (e.g., up to about 20 mm).

The receiver transponder 2530 includes or is electrically coupled to one or more sensors 2540, which are configured to measure a physical property of the interior of the pipe 2510. For example, the sensors 2540 can measure the temperature of a substance, such as a fluid (e.g., gas and/or liquid), flowing through pipe 2510. The sensors 2540 can also measure the chemical composition of the fluid, the internal pressure of the pipe 2510 or fluid, or other physical properties of the interior of the pipe 2510 (e.g., fluid (gas or liquid) viscosity), flow shear forces, flow turbulence, etc.). The receiver transponder 2530 is encapsulated with a protective layer, such as a thin metal shim (e.g., such as steel or Ti). The encapsulation can also include a metal housing, an epoxy encapsulation, a potted epoxy encapsulation, or a plastic injection molded enclosure. As a result of the encapsulation only the sensors 2540 are exposed to the interior of the pipe 2510.

In operation, the transceiver 2520 generates ultrasound energy through one or more electroacoustic transmitting elements 2522 (e.g., ultrasound transducers), which may be disposed in convex configuration (e.g., as illustrated in FIG. 35). As in the embodiments discussed above, the transceiver 2520 can generate a standing wave (and/or progressive longitudinal waves and/or shear waves) of ultrasound energy that optimizes power transfer and that provides a carrier wave that can be modulated to transmit information or commands. In some embodiments, a high energy node of the standing wave of ultrasonic energy is disposed at the receiver transponder 2530.

The ultrasound energy passes through the metallic wall 2512 of the pipe 2510 and is received by one or more electroacoustic receiving elements 2532 (e.g., ultrasound transducers) on the receiver transponder 2530, which converts the ultrasound energy to electrical energy in the manner discussed above. The electroacoustic receiving elements 2532 can be disposed in a concave configuration (e.g., as illustrated in FIG. 35). The converted electrical energy is then used to power the sensors 2540 either directly or indirectly (e.g., by charging a battery coupled to the sensors 2540). Physical sensor data from the sensors can be transmitted back to the transceiver 2520 by keyed acoustical impedance changes of the ultrasound energy harvesting by receiver transponder 2530 (e.g., as discussed above). The transceiver 2520 can transmit the physical sensor data to a controller, a central processing unit, or other device via an antenna 2524 (e.g., an RF antenna) on the transceiver 2520.

FIG. 26A is a cross section of a system 2600 for providing ultrasonic energy and converted electrical power to a sensor in a vessel 2610 having a metallic wall 2612. The system 2600 includes an ultrasound transceiver 2620 and an ultrasound receiver transponder 2630. The ultrasound transceiver 2620 is mounted on a first end 2652 of a metal rod 2650 and the receiver transponder 2630 is mounted on a second end 2654 of the metal rod 2650. As illustrated, the second end 2654 of the metal rod 2650 is disposed in the internal cavity 2615 of vessel 2610, which may include a fluid or other substance that may be environmentally harsh (e.g., due to its temperature, pressure, chemical composition, etc.). The metal rod 2650 can be circular, oval, rectangular, square, triangular or other shape in cross section.

The ultrasound transceiver 2620 includes one or more electroacoustic transmitting elements 2622 (e.g., ultrasound transducers) coupled to electronics 2624, which can include a signal generator, an amplifier, and a controller, and other components similar to DTMS 1600 illustrated in FIG. 16. A detailed view 2680 of the ultrasound transceiver 2620, including the flow of ultrasonic energy, is illustrated in FIG. 26B.

The receiver transponder 2630 includes one or more electroacoustic receiving elements 2632 (e.g., ultrasound transducers) coupled to electronics 2634, which can include a rectifier, a capacitor, and a controller similar to DTMS 1600 illustrated in FIG. 16. The electronics 2634 are also coupled to one or more sensors 2640, which can measure a physical property of the internal cavity of vessel 2610, including a fluid, a chemical, or an object disposed therein. A detailed view 2690 of the receiver transponder 2630, including the flow of ultrasonic energy, is illustrated in FIG. 26C. The receiver transponder 2630 is encapsulated with a protective layer such that only the sensors 2640 are exposed to the interior of the vessel 2610. The encapsulation can be the same as the encapsulation for receiver transponder 2530, discussed above.

In operation, the transceiver 2620 generates ultrasound energy through one or more electroacoustic transmitting elements 2622 (e.g., ultrasound transducers). As in the embodiments discussed above, the transceiver 2620 can generate a standing wave (and/or progressive longitudinal waves and/or shear waves) of ultrasound energy that optimizes power transfer and that provides a carrier wave that can be modulated to transmit information or commands. In some embodiments, a high energy node of the standing wave of ultrasonic energy is disposed at the receiver transponder 2630.

The ultrasound energy passes along the rod 2650 and is received by one or more electroacoustic receiving elements 2632 (e.g., ultrasound transducers) on the receiver transponder 2630, which converts the ultrasound energy to electrical energy in the manner discussed above. The converted electrical energy is then used to power the sensors 2640 either directly or indirectly (e.g., by charging a battery coupled to the sensors 2640). Physical sensor data from the sensors can be transmitted back to the transceiver 2620 by keyed acoustical impedance changes of the ultrasound energy harvesting by receiver transponder 2630 (e.g., as discussed above). The transceiver 2620 can transmit the physical sensor data to a controller, a central processing unit, or other device via an antenna 2626 (e.g., an RF antenna) on the transceiver 2620.

FIG. 27 is a cross section of a system 2700 for providing ultrasonic energy and converted electrical power to a sensor in an enclosure or housing 2710 (in general, enclosure 2710) having a metallic wall 2712. The system 2700 includes an ultrasound transceiver 2720 and an ultrasound receiver transponder 2730. The ultrasound transceiver 2720 is mounted on an external surface 2714 of a wall 2712 of enclosure 2710. The ultrasound receiver transponder 2730 is mounted on an internal surface 2716 of the wall 2712 of enclosure 2710. The transceiver 2720 and the receiver transponder 2730 are aligned on the wall 2712 of the enclosure 2710. For example, the transceiver 2720 can be disposed at a transceiver location on the external surface 2714 of the wall 2712 and the receiver transponder 2730 can be disposed at a transponder location on the internal surface 2716 of the wall 2712, where the transceiver location corresponds to the transponder location. In some embodiments, the transceiver location and the transponder location are on opposing sides of the wall 2712, for example as illustrated in FIG. 27. The wall 2712 can be thick (e.g., up to about 40 mm) and can be comprised of a dense material, such as a metal, plastic, stone, ceramics, or composites of the foregoing.

The receiver transponder 2730 includes or is electrically coupled to one or more sensors 2740, which are configured to measure a property of an object 2760 in the enclosure 2710. The object 2760 can be a potentially harmful object, for example a potentially radioactive object, an explosive, or other object. For the Timely Hybrid Radio Frequency-Ultrasound Technique (TRUST), the sensors 2740 can include an RF transponder that can perform a still or moving scan 2745 analogous to that used in phased array radar to sense the shape of the object 2760, which may be metal, in the enclosure 2710. In addition or in the alternative, the sensors 2740 can measure the chemical composition, heat output (e.g., from nuclear radiation), moisture content (e.g., from organic material), or other property of object 2760.

In operation, the transceiver 2720 generates ultrasound energy through one or more electroacoustic transmitting elements 2722 (e.g., ultrasound transducers). As in the embodiments discussed above, the transceiver 2720 can generate a standing wave (and/or progressive longitudinal waves and/or shear waves) of ultrasound energy that optimizes power transfer and that provides a carrier wave that can be modulated to transmit information or commands. In some embodiments, a high energy node of the standing wave of ultrasonic energy is disposed at the receiver transponder 2730.

The ultrasound energy passes through the metallic wall 2712 of the enclosure 2710 and is received by one or more electroacoustic receiving elements 2732 (e.g., ultrasound transducers) on the receiver transponder 2730, which converts the ultrasound energy to electrical energy in the manner discussed above. The converted electrical energy is then used to power the sensors 2740 either directly or indirectly (e.g., by charging a battery coupled to the sensors 2740). Physical sensor data from the sensors can be transmitted back to the transceiver 2520 by keyed acoustical impedance changes (e.g., via load changes of the receiver transducer) of the ultrasound energy harvesting by receiver transponder 2730 (e.g., as discussed above). The transceiver 2720 can transmit the physical sensor data to a controller, a central processing unit, or other device via an antenna (e.g., an RF antenna) on the transceiver 2720. As in the above embodiments, the transceiver 2720 includes electronics 2724 electrically coupled to the one or more electroacoustic transmitting elements 2722 and the receiver transponder 2730 includes electronics 2734 electrically coupled to the one or more electroacoustic receiving elements 2732.

FIG. 28 is a block diagram of a system 2800 for recharging a battery for an ultrasonic transponder disposed in a body of water. The system 2800 includes an autonomous underwater vehicle (AUV) or a remote operating vehicle (ROV) (in general, AUV 2810). The AUV is retrofitted with a retractable probe having an ultrasound charging module, the transmitter, located distally at the end of this probe. This appendage is termed as an ultrasound energy recharging stinger (US-Stinger) 2820. The US-Stinger includes an electromechanical interface 2830 (which can be pressure balanced and oil-filled (PBOF)), wire pigtails (e.g., insulated and sealed connectors on the physical docking interface), a housing, an ultrasonic transmitter, drive electronics (e.g., as discussed above), and digital control/communication circuits.

The AUV 2810 utilizes and on-board power management system (PMS) and navigation (NAV) system to identify, activate and communicate with the US-Stinger components, either through hard-wired contact, or wirelessly using RF energy. This capability enables the setting of various parameters and charging protocols for a particular stationary sub-sea data control set up. The AUV mates with the stationary sub-sea data station periodically (over 15-90 days), and through the US-Stinger 2820, which has mated with the US-Coupler Receiver, the stationary controller batteries are charged up to enable interruption-free operation of various functions, and to maintain acceptable data transfer rates. In addition, through the US-Stinger 2820, specific updated operational protocols can also be loaded on to the stationary instrument controller on the sea floor. Bidirectional communication between the US-Stinger 2820 and the US-Coupler Receiver can occur in the same manner as in other embodiments described herein. The US-Stinger 2820 can have a retractable mechanism to be deployed when the AUV 2810 comes in proximity to the stationary control panel.

The ultrasound receiver (US-Receiver) 2840 is installed on a stationary control unit 2850, which mates with the ultrasonic transmitter from the AUV 2810 on a periodic basis. The US-Receiver includes an electromechanical mating interface 2860 (with appropriate coupling medium, such as PBOF). The receiver ultrasound ceramics are installed, with rectifier and data communication circuitry, and wire pigtails. The US-Receiver stationary control unit is electrically coupled to a configured battery or an appropriate energy accumulator capability to power an instrument module coupled to the US-Receiver 2840.

FIG. 29 is a diagrammatic cross-sectional view of a system 2900 for providing ultrasonic energy and converted electrical power to a sensor along a drill string coupled to an above surface coupler, Kelly drive 2950. The system 2900 includes an ultrasound transceiver 2920 and an ultrasound receiver transponder 2930. The ultrasound transceiver 2920 is mounted on the Kelly drive body 2952. The ultrasound receiver transponder 2930 is mounted on a proximal end 2962 of bottom hole assembly (BHA) 2960. A drill string 2970 extends from the Kelly drive 2950 through at least a portion of the BHA 2960.

In operation, the transceiver 2920 generates ultrasound energy through one or more electroacoustic transmitting elements 2922 (e.g., ultrasound transducers), which are coupled to electronics 2924 (e.g., as discussed above). As in the embodiments discussed above, the transceiver 2920 can generate a standing wave (and/or progressive longitudinal waves and/or shear waves) of ultrasound energy that optimizes power transfer and that provides a carrier wave that can be modulated to transmit information or commands. In some embodiments, a high energy node of the standing wave of ultrasonic energy is disposed at the receiver transponder 2930. The ultrasound energy generated by the transceiver 2920 passes through the Kelly drive body 2952 including bearings 2954, the drill string 2970, and the BHA 2960 until it reaches the receiver transponder 2930, similar to the manner discussed herein. The ultrasound energy is received by one or more electroacoustic receiving elements 2932 (e.g., ultrasound transducers) on the receiver transponder 2930, coupled to electronics 2934 (e.g., as discussed above), which converts the ultrasound energy to electrical energy in the manner discussed above. The converted electrical energy is then used to power one or more sensors 2940 either directly or indirectly (e.g., by charging a battery coupled to the sensors 2940). Physical sensor data from the sensors can be transmitted back to the transceiver 2920 by keyed acoustical impedance changes (e.g., load changes of the receiver transducer) of the ultrasound energy harvesting by receiver transponder 2930 (e.g., as discussed above). The transceiver 2920 can transmit the physical sensor data to a controller, a central processing unit, or other device via an antenna (e.g., an RF antenna) on the transceiver 2920. Examples of physical sensor data include fluid (gas or liquid) viscosity, flow shear forces, flow turbulence, vibration, vibrational directions (e.g., in the xyz coordinates), acceleration, acceleration directions (e.g., in the xyz coordinates), audio sound made by the drill head nearby (characterization of drilling process in formation), lateral and radial stress on the pipe.

FIG. 30 is a top view of a transducer array 3000 that can be used in system 2900. The transducer array 3000 includes a plurality of electroacoustic transmitting or receiving elements 3010 disposed in a housing 3020. The transducer array 3000 can be incorporated in system 2900 as the one or more electroacoustic transmitting elements 2922 and/or as the one or more electroacoustic receiving elements 2932.

FIG. 31 is a flow chart 3100 for providing ultrasonic energy and converted electrical power to a sensor in a metallic pipe or in a metallic vessel. Flow chart 3100 can be practiced with systems 2500 and 2600 (illustrated in FIGS. 25 and 26, respectively), discussed above. In step 3110, the ultrasound transceiver (e.g., transceiver 2520) establishes communication with the receiver transponder (e.g., receiver transponder 2530). This step includes energizing the ultrasound transceiver, transmitting ultrasound energy, energizing the receiver transponder, modulating ultrasound with the receiver transponder's address and wake-up code, transmitting commands, and listening to the receiver transponder's response via impedance changes. Examples of modulating ultrasound include amplitude, frequency, phase, quadrature, space, and/or single-sideband modulations. Additional examples of modulating ultrasound include analog modulation schemes such as amplitude-shift keying, amplitude and phase-shift keying, continuous phase, frequency-shift keying, on-off keying, pulse-position, phase-shift keying, quadrature amplitude, etc. Inputs 3105 to step 3110 include the receiver transponder's address, the wake-up code for the receiver transponder, and control commands for the receiver transponder. Outputs 3115 to step 3110 include the system status (e.g., the receiver transponder's status), the receiver transponder's response, and data (e.g., response data) from the receiver transponder.

In step 3120, the ultrasound transceiver (or a controller coupled thereto) determines if the receiver transponder responded correctly. If the transceiver responder did not respond correctly in step 3120, the outputs 3115 are provided, which can be used to determine why the receiver responder did not respond correctly. If the receiver responder responded correctly in step 3120, the ultrasound transceiver interrogates the receiver transponder in step 3130. The interrogation step 3130 includes sending commands for a status inquiry of the receiver transponder, receiver transponder configuration, receiver transponder operation, and data requests (e.g., sensor data) for the receiver transponder. In response, the receiver transponder transmits (e.g., by impedance modulation) its status and the requested data, which are received by the ultrasound transceiver. Inputs 3125 to step 3130 include commands for the ultrasound transceiver to send to the receiver transponder for its status inquiry, to configure the receiver transponder and its operation, and for requesting data readout. Outputs 3135 to step 3130 include the receiver transponder's status and the data (e.g., sensor data) acquired by the receiver transponder.

FIG. 32 is a flow chart 3200 for providing ultrasonic energy and converted electrical power to a sensor in a metallic enclosure. Flow chart 3200 can be practiced with system 2700 (illustrated in FIG. 27), discussed above. In general, flow chart 3200 is substantially the same as flow chart 3100 with the differences noted below. For example, steps 3205, 3210, 3215, and 3220 are the same or substantially the same as steps 3105, 3110, 3115, and 3120, respectively. In step 3230, the ultrasound transceiver interrogates the receiver responder by sending commands for a status inquiry, receiver transponder configuration, receiver transponder operation, and data requests (e.g., sensor data) for the receiver transponder. In response, the receiver transponder transmits (e.g., by impedance modulation) its status and the requested data, which are received by the ultrasound transceiver. Inputs 3225 to step 3230 include commands for the ultrasound transceiver to send to the receiver transponder for its status inquiry, to configure the receiver transponder and its operation, for RF scanning, position sensing, and requesting data readout. Outputs 3235 to step 3230 include the receiver transponder's status and the data (e.g., sensor data) acquired by the receiver transponder.

FIG. 33 is a flow chart 3300 for recharging a battery for an ultrasonic transponder disposed in a body of water. Flow chart 3300 can be practiced with system 2800 (illustrated in FIG. 28), discussed above. Since the US-Stinger unit is appended to the AUV, in step 3310, the AUV/ROV uses its PMS and NAV systems to identify and communicate with a US Stinger, through either a hardwired or a RF communication link, and to record any error codes. Inputs 3305 to step 3310 include the US Stinger communication protocol and the system error protocol. Outputs 3315 to step 3310 include the system status (e.g., establishing that the US-Stinger attachment is operating as intended) and any error codes.

In step 3320, the AUV/ROV determines if the US Stinger responded without any error codes. If not, the flow chart 3300 proceeds to step 3315 to evaluate the error codes to determine the source of the error. If no error codes are received, the flow chart 3300 proceeds to step 3330 to establish communication with the subsea control unit. This step includes docking the AUV/ROV at the target site, initiating a communication protocol with the subsea control unit, and recording any error codes. Inputs 3325 to step 3330 include the subsea control unit's address, the communication protocol for communicating with the subsea control unit, and the system error protocol. Outputs 3335 to step 3330 include the subsea control unit's status and any error codes from the subsea control unit.

In step 3340, the AUV/ROV determines whether the subsea control unit responds without any error codes. If not, the flow chart 3300 proceeds to step 3335 to evaluate the error codes to determine the source of the error. If no error codes are received, the flow chart 3300 proceeds to step 3350 to deliver power and communicate with the subsea control unit. Step 3350 includes transmitting ultrasound energy and commands, reading data, recording any error codes, and terminating when the batteries are fully charged. Inputs 3345 to step 3350 include the subsea control unit commands. Outputs 3355 to step 3350 include the system status (e.g., the subsea control unit's status), any error codes, and data from the subsea control unit (e.g., battery charge status).

FIG. 34 is a flow chart 3400 for providing ultrasonic energy and converted electrical power to a sensor (e.g., in a BHA) along a drill string coupled to a Kelly drive coupler. Flow chart 3400 can be practiced with system 2900 (illustrated in FIG. 29), discussed above. In step 3410, the ultrasound transceiver establishes communication with the transceiver responder(s) disposed on the BHA. Step 3410 includes energizing the ultrasound transceiver, transmitting ultrasound energy along the drill string to the receiver transponder(s), activating the receiver transponder(s) operation, modulating the ultrasound with the respective receiver transponder's address and wake-up code, transmitting commands from the ultrasound transceiver to the respective receiver transponder (e.g., by modulating the ultrasound), and listening to the respective receiver transponder's response via impedance changes. Inputs 3405 to step 3410 include the receiver transponder's address (e.g., if there is more than one receiver transponder at the BHA), the wake-up code(s) for the receiver transponder(s), and the commands for the receiver transponder(s). Outputs 3415 to step 3410 include the system status (e.g., the status of the receiver transponder(s)), the response from the receiver transponder(s), and the data (e.g., sensor data) from the receiver transponder(s).

In step 3420, the ultrasound transceiver determines if the receiver transponder(s) responded correctly. If not, the flow chart 3400 returns to step 3415 to evaluate the system status and/or error codes to determine the source of the error. If the receiver transponder(s) responded correctly, the flow chart 3400 proceeds to step 3430 to interrogate the receiver transponder(s). Interrogating the receiver transponder 3430 includes sending commands from the ultrasound transceiver to the respective receiver transponder, such as commands for a status inquiry of the receiver transponder, configuration of the receiver transponder, operation of the receiver transponder, and data (e.g., sensor data) readout requests from the receiver transponder. Inputs 3425 to step 3430 include the commands for a status inquiry of the receiver transponder, configuration of the receiver transponder, operation of the receiver transponder, and data (e.g., sensor data) readout requests from the receiver transponder. Outputs 3435 to step 3430 include the respective receiver transponder's status and the data (e.g., sensor data) readout from the receiver transponder.

Though the foregoing figures have illustrated sensor systems for measuring tire pressure and or measuring properties of a shock absorber, it is noted that these are just exemplary locations for such sensor systems. Thus, the ultrasonic-powered sensors can be located in other locations in the vehicle (e.g., in or proximal to the exhaust system, the cooling system, etc.) or in other systems, such as industrial systems, airplanes, etc. In addition, the term vehicle can include passenger vehicles, trucks, construction equipment, motorcycles, and other self-propelled vehicles, whether powered by gasoline, electricity, or a combination thereof. Another application of the foregoing systems is in underwater vehicles, boats, submarines, etc.

Ultrasound spans a large range of frequencies, from roughly 20 KHz out to hundreds of MHz. Frequencies below about 100 kHz are characterized by less absorption in air, larger ultrasound transmitters, longer wavelengths and wider cone angles into which the ultrasound is transmitted. The latter can be reduced by using arrays of transmitters emitting coherently, which also can be used to turn or focus ultrasound radiation. However these arrays will tend to be bulky. Frequencies above 100 kHz are characterized by being strongly absorbed by air, have more compact transmitters, more collimated radiation in the near and mid-fields, and shorter wavelengths.

While the former regime is appealing for the prospect of transmitting wireless power through air to many receivers, it also brings up questions of safety because people will be irradiated by the generally uncollimated beams. Also because the radiation will typically be emitted into a cone some 10 or 20 or more degrees in angular width, much of the transmitted power will miss receivers, requiring high power transmitters, so that some energy is incident on small receivers, again bringing up the issue of safety. Small electronics that have incident high power vibrational amplitudes could be damaged. Hence any scheme for ultrasound delivery through air in locations where humans are generally present may be rejected on the basis of safety and its effect on people and materials.

Some embodiments use frequencies in the 500 kHz to 1 to 2 MHz range. Other embodiments apply ultrasound in a range between 20 kHz and 100 kHz, depending on the application at hand. Also advantageous will be charging geometries that bring the transmitter close to the receiver, within 1 cm or less, with the two possibly separated by a thin flexible pad that excludes air. This type of arrangement ensures that no ultrasound radiation escapes the charging path and that much lower transmitted powers can be used because there is little power lost in side lobes. Narrowing this band of frequencies or choosing specific small frequency bands will depend on details of construction that minimize reflections, match ultrasound impedances for the materials used and optimize useful power transfer.

The present system and method may be applied to powering or charging automobile sensors at frequencies in the sub-100 kHz range, avoiding transmission into the driver/passenger compartment, thereby eliminating safety or electronic interference issues. Other applications hereof may be in underwater vehicles and systems. The ultrasound energy may propagate in these applications through liquid filled bladders, and then wirelessly to the device or battery under charge or power. In an aspect, the transceiver of the present system comprises an antenna to electrically communicate with a central processing unit.

In an aspect, the transmitted ultrasonic signals are received by said electroacoustic receiving elements of the system.

In yet another aspect, the transponder of the present system converts said transmitted ultrasonic signals into converted electrical energy.

In yet another aspect, the sensor of the present system is powered by said converted electrical energy.

In an aspect, the ultrasound receiver of the present system converts said transmitted ultrasonic signals into converted electrical energy.

In still another aspect, a stationary control unit of the present system is electrically coupled to a battery; and, the battery powers an instrument module.

And in an aspect, the sensor of the present system is powered by said converted electrical energy.

The embodiments described and illustrated herein are not meant by way of limitation, and are rather exemplary of the kinds of features and techniques that those skilled in the art might benefit from in implementing a wide variety of useful products and processes. For example, in addition to the applications described in the embodiments relating to power transmission and conversion for use in battery charging, those skilled in the art would appreciate that the present disclosure can be applied to any electroacoustic direct power topologies. However, it is to be appreciated that the present exemplary embodiments are also amenable to other like applications.

The present invention should not be considered limited to the particular embodiments described above, but rather should be understood to cover all aspects of the invention as fairly set out in the attached claims. Various modifications, equivalent processes, as well as numerous structures, materials and unforeseen technologies to which the present invention may be applicable, will be readily apparent to those skilled in the art to which the present invention is directed upon review of the present disclosure. The claims are intended to cover such modifications and equivalents.

What is claimed is:

1. A system for sensing a physical property inside a pipe having a metallic wall, the system comprising:
 a transceiver mounted at a transceiver location on an external surface of the metallic wall, the transceiver comprising:

one or more electroacoustic transmitting elements;
a signal generator; and
an amplifier;
a transponder mounted at a transponder location on an internal surface of the metallic wall, the transponder comprising:
one or more electroacoustic receiving elements; and
a sensor that measures the physical property of an interior environment of the pipe,
wherein said electroacoustic transmitting and receiving elements are in bi-directional ultrasonic communication such that the transponder is configured to communicate physical sensor data, received from the sensor, to the transceiver, and
wherein the one or more electroacoustic transmitting elements are arranged in a convex configuration and the one or more electroacoustic receiving elements are arranged in a concave configuration.

2. The system of claim 1, wherein said transponder is configured to vary an acoustical impedance to communicate the physical sensor data to the transceiver.

3. The system of claim 1, wherein signals are generated by said signal generator and amplified by said amplifier, said amplified signals are transmitted over said one or more electroacoustic transmitting elements, said one or more electroacoustic transmitting elements generating acoustic energy that passes from said transceiver to said transponder via said metallic wall.

4. The system of claim 3, wherein the transponder location is aligned with the transceiver location.

5. The system of claim 1, wherein the transceiver is configured to generate a standing wave of ultrasonic energy.

6. The system of claim 5, wherein a high-energy node of the standing wave is disposed at the transponder.

7. A system for providing electrical energy to a sensor disposed in an enclosure having a metallic wall, the system comprising:
a transceiver mounted at a transceiver location on an external surface of the metallic wall, the transceiver comprising:
one or more electroacoustic transmitting elements that generate acoustic energy;
a signal generator; and
an amplifier;
a transponder mounted at a transponder location on an internal surface of the metallic wall, the transponder comprising:
one or more electroacoustic receiving elements that convert the acoustic energy into electrical energy; and
a sensor that measures a physical property of an object disposed in the enclosure,
wherein said electroacoustic transmitting and receiving elements are in bi-directional ultrasonic communication such that the transponder is configured to communicate physical sensor data, received from the sensor, to the transceiver, and
wherein the sensor comprises an RF transponder, and
wherein the RF transponder is configured to perform a scan of an interior of the enclosure to sense a shape of the object.

8. The system of claim 7, wherein the sensor measures a chemical composition, a heat output, or a moisture content of the object.

9. The system of claim 7, wherein said transponder is configured to vary an acoustical impedance to communicate the physical sensor data to the transceiver.

10. The system of claim 7, wherein the transceiver comprises an antenna to electrically communicate with a central processing unit.

11. The system of claim 7, wherein signals are generated by said signal generator and amplified by said amplifier, said amplified signals are transmitted over said one or more electroacoustic transmitting elements, said one or more electroacoustic transmitting elements generating acoustic energy that passes from said transceiver to said transponder via said metallic wall.

12. The system of claim 11, wherein the transponder location is aligned with the transceiver location.

13. The system of claim 7, wherein the sensor is powered by said electrical energy.

14. The system of claim 7, wherein the transceiver is configured to generate a standing wave of ultrasonic energy.

15. The system of claim 14, wherein a high-energy node of the standing wave is disposed at the transponder.

* * * * *